(12) United States Patent
White

(10) Patent No.: US 11,039,918 B2
(45) Date of Patent: Jun. 22, 2021

(54) REPOSITIONABLE ENDOLUMINAL SUPPORT STRUCTURE AND ITS APPLICATIONS

(71) Applicant: Edwards Lifesciences CardiAQ LLC, Irvine, CA (US)

(72) Inventor: Jennifer K. White, Charlestown, RI (US)

(73) Assignee: Edwards Lifesciences CardiAQ LLC, Irvine, CA (US)

(*) Notice: Subject to any disclaimer, the term of this patent is extended or adjusted under 35 U.S.C. 154(b) by 616 days.

(21) Appl. No.: 15/801,212

(22) Filed: Nov. 1, 2017

(65) Prior Publication Data

US 2018/0055634 A1     Mar. 1, 2018

Related U.S. Application Data

(60) Continuation of application No. 15/157,337, filed on May 17, 2016, now Pat. No. 10,292,842, which is a
(Continued)

(51) Int. Cl.
*A61F 2/24*     (2006.01)
*A61F 2/82*     (2013.01)
(Continued)

(52) U.S. Cl.
CPC .............. *A61F 2/2418* (2013.01); *A61F 2/24* (2013.01); *A61F 2/243* (2013.01); *A61F 2/2409* (2013.01);
(Continued)

(58) Field of Classification Search
CPC .... A61F 2/2409; A61F 2/2412; A61F 2/2418; A61F 2/2427; A61F 2/243; A61F 2/24; A61F 2/2421; A61F 2/2469; A61F 2/844
See application file for complete search history.

(56) References Cited

U.S. PATENT DOCUMENTS 3,548,417 A    12/1970   Kisher
5,242,451 A     9/1993   Harada et al.
(Continued)

FOREIGN PATENT DOCUMENTS

EP     2138132 A2    12/2009
JP     3118078 B2    12/2000
(Continued)

*Primary Examiner* — William H Matthews
(74) *Attorney, Agent, or Firm* — Klarquist Sparkman, LLP; Joel B. German

(57) ABSTRACT

A prosthetic heart valve includes a frame, a valve component, and a skirt. The frame has first and second end portions, a central longitudinal axis extending between the first and second end portions, and a plurality of struts interconnected by a plurality of joints. The joints comprise a rotational axis perpendicular to the longitudinal axis. The frame is movable between an expanded configuration and a compressed configuration. The struts comprise diagonal struts relative to the longitudinal axis when the frame is in the expanded configuration. The valve component has a plurality of leaflets. Adjacent leaflets are attached together and to the frame at commissures of the frame. The leaflets extend from the commissures in a triangular configuration and are attached to adjacent diagonal struts of the frame. The skirt is configured for reducing paravalvular leakage and attached to the diagonal struts of the frame to which the leaflets are attached.

20 Claims, 21 Drawing Sheets

Related U.S. Application Data division of application No. 13/113,890, filed on May 23, 2011, now Pat. No. 9,364,323, which is a continuation of application No. 12/761,295, filed on Apr. 15, 2010, now Pat. No. 8,226,707, which is a continuation of application No. PCT/US2009/051324, filed on Jul. 21, 2009.

(60) Provisional application No. 61/082,489, filed on Jul. 21, 2008.

(51) Int. Cl.
  *A61F 2/844* (2013.01)
  *A61F 2/94* (2013.01)

(52) U.S. Cl.
  CPC .......... *A61F 2/2412* (2013.01); *A61F 2/2421* (2013.01); *A61F 2/2427* (2013.01); *A61F 2/2469* (2013.01); *A61F 2/844* (2013.01); *A61F 2/94* (2013.01); *A61F 2/82* (2013.01); *A61F 2210/0076* (2013.01); *A61F 2220/0041* (2013.01); *A61F 2220/0075* (2013.01); *A61F 2230/0054* (2013.01); *A61F 2230/0091* (2013.01); *A61F 2250/001* (2013.01); *A61F 2250/0004* (2013.01); *Y10T 29/49826* (2015.01)

(56) References Cited

U.S. PATENT DOCUMENTS

| | | | |
|---|---|---|---|
| 5,280,789 A | 1/1994 | Potts | |
| 5,339,810 A | 8/1994 | Ivers et al. | |
| 5,388,619 A | 2/1995 | Ghawi | |
| 5,554,183 A | 9/1996 | Nazari | |
| 5,797,951 A | 8/1998 | Mueller | |
| 5,855,565 A | 1/1999 | Bar-Cohen et al. | |
| 5,871,536 A | 2/1999 | Lazarus | |
| 6,224,626 B1 | 5/2001 | Steinke | |
| 6,267,783 B1 | 7/2001 | Letendre et al. | |
| 6,558,396 B1 | 5/2003 | Inoue | |
| 6,656,215 B1 | 12/2003 | Yanez et al. | |
| 6,669,720 B1 | 12/2003 | Pierce | |
| 6,716,230 B2 | 4/2004 | Whitman | |
| 6,730,118 B2 | 5/2004 | Spenser et al. | |
| 6,730,121 B2 | 5/2004 | Ortiz et al. | |
| 6,733,525 B2 | 5/2004 | Yang et al. | |
| 6,761,733 B2 | 7/2004 | Chobotov et al. | |
| 6,773,456 B1 | 8/2004 | Gordon et al. | |
| 6,860,900 B2 | 3/2005 | Clerc et al. | |
| 6,890,350 B1 | 5/2005 | Walak | |
| 6,893,460 B2 | 5/2005 | Spenser et al. | |
| 6,929,659 B2 | 8/2005 | Pinchuk | |
| 6,945,994 B2 | 9/2005 | Austin et al. | |
| 6,951,571 B1 | 10/2005 | Srivastava | |
| 7,007,396 B2 | 3/2006 | Rudko et al. | |
| 7,011,681 B2 | 3/2006 | Vesely | |
| 7,041,132 B2 | 5/2006 | Quijano et al. | |
| 7,090,688 B2 | 8/2006 | Nishtala et al. | |
| 7,097,658 B2 | 8/2006 | Oktay | |
| 7,141,063 B2 | 11/2006 | White et al. | |
| 7,556,646 B2 | 7/2009 | Yang et al. | |
| 7,731,742 B2 | 6/2010 | Schlick et al. | |
| 8,252,036 B2 | 8/2012 | Cartledge et al. | |
| 8,430,925 B2 | 4/2013 | Forster et al. | |
| 8,460,368 B2 | 6/2013 | Taylor et al. | |
| 8,647,378 B2 | 2/2014 | Mews et al. | |
| 8,673,001 B2 | 3/2014 | Cartledge et al. | |
| 8,685,055 B2 | 4/2014 | VanTassel et al. | |
| 2002/0077695 A1 | 6/2002 | Swanson et al. | |
| 2003/0040791 A1 | 2/2003 | Oktay | |
| 2003/0050694 A1 | 3/2003 | Yang et al. | |
| 2003/0120331 A1 | 6/2003 | Chobotov et al. | |
| 2006/0173527 A1 | 8/2006 | Scherrible | |
| 2006/0259136 A1 | 11/2006 | Nguyen et al. | |
| 2008/0009746 A1 | 1/2008 | Forster et al. | |
| 2009/0030501 A1 | 1/2009 | Morris et al. | |
| 2012/0150289 A1 | 6/2012 | Forster et al. | |
| 2012/0323316 A1 | 12/2012 | Chau et al. | |
| 2013/0046373 A1 | 2/2013 | Cartledge et al. | |

FOREIGN PATENT DOCUMENTS

| | | |
|---|---|---|
| JP | 6483251 B2 | 3/2019 |
| WO | 9913800 A1 | 3/1999 |
| WO | 02074398 A1 | 9/2002 |
| WO | 03018100 A1 | 3/2003 |
| WO | 03047468 A1 | 6/2003 |
| WO | 2005084595 A1 | 9/2005 |
| WO | 2005094952 A1 | 10/2005 |
| WO | 2006105084 A2 | 10/2006 |
| WO | 2007138608 A1 | 12/2007 |
| WO | 2008015257 A2 | 2/2008 |

REPOSITIONABLE ENDOLUMINAL SUPPORT STRUCTURE AND ITS APPLICATIONS

RELATED APPLICATIONS

This application is a continuation of U.S. patent application Ser. No. 15/157,337, filed May 17, 2016, which is a divisional of U.S. patent application Ser. No. 13/113,890, filed May 23, 2011, now U.S. Pat. No. 9,364,323, which is a continuation of U.S. patent application Ser. No. 12/761,295, filed Apr. 15, 2010, now U.S. Pat. No. 8,226,707, which is a continuation of PCT Application No. PCT/US2009/051324, filed Jul. 21, 2009, which claims the benefit of U.S. Provisional Application No. 61/082,489, filed Jul. 21, 2008, all of which are incorporated by reference herein in their entireties.

BACKGROUND

Endoluminal stents can be implanted in a vessel or tract of a patient to help maintain an open lumen. The stents can also be used as a frame to support a prosthetic device or to deliver a therapeutic agent. Stents can be implanted by either an open operative procedure or a closed operative procedure. When an option exists, the less invasive closed procedure is generally preferred because the stent can be guided through a body lumen, such as the femoral artery, to its desired location.

Closed procedures typically use one of two techniques. One closed procedure employs balloon catheterization where an expandable stent encloses an inflatable balloon. In this procedure, the stent is implanted by inflating the balloon, which causes the stent to expand. The actual positioning of the stent cannot be determined until after the balloon is deflated and, if there is a misplacement of the stent, the process cannot be reversed to reposition the stent.

The other closed procedure employs a compressed stent enclosed by a removable sheath. In this procedure, a stent made from a shape memory alloy, such as Nitinol, is held in a compressed state by a sheath. The stent is implanted by withdrawing the sheath, causing the stent to expand to its nominal shape. Again, if there is a misplacement of the stent, the process cannot be reversed to reposition the stent.

Positioning errors are particularly dangerous when the stent is used to support a cardiac valve. Serious complications and patient deaths have occurred due to malpositioning of the valve at the implant site in the body, using the available stent-mounted valves. Malpositioning of the valve has resulted in massive paravalvular leakage, device migration, and coronary artery obstruction. The majority of these complications were unavoidable, but detected at the time of the procedure. However, due to inability to reposition or retrieve the device, these problems were impossible to reverse or mitigate during the procedure.

SUMMARY

An endoluminal support structure or stent in accordance with certain embodiments of the invention solves certain deficiencies found in the prior art. In particular, the support structure can be repositioned within the body lumen or retrieved from the lumen.

A particular embodiment of the invention includes a support apparatus implantable within a biological lumen. The support apparatus can include a plurality of elongated strut members interlinked by a plurality of swivel joints, wherein the swivel joints can cooperate with the stent members to adjustably define a shaped structure between a compressed orientation and an expanded orientation.

More particularly, the shaped structure can be one of a cylindrical, a conical, or an hourglass shape. A swivel joint can form a scissor mechanism with a first strut member and a second strut member. Furthermore, the strut members can be arranged as a series of linked scissor mechanisms. The apparatus can further include an actuation mechanism to urge the swivel joints within a range of motion.

The apparatus can also include a prosthetic valve coupled to the shaped structure.

Another particular embodiment of the invention can include a medical stent implantable within a biological lumen. The medical stent can include a plurality of elongated strut members, including a first strut member and a second strut member, and a swivel joint connecting the first strut member and the second strut member.

In particular, the swivel joint can form a scissor mechanism with the first strut member and the second strut member. The swivel joint can bisect the first strut member and the second strut member. The swivel joint can interconnect a first end of the first strut member with a first end of the second strut member.

The plurality of strut members can be arranged as a series of linked scissor mechanisms. The strut members can also be non-linear. The strut members can be arranged to form one of a cylindrical, a conical, or an hourglass shape.

The stent can further include an adjustment mechanism to exerting a force to urge the strut members about the swivel joint within a range of motion.

The stent can include a prosthetic valve coupled to the strut members.

Specific embodiments of the invention can include prosthetic valves that are rotatable or conventional.

A rotatable prosthetic valve can include a first structural member coupled to the strut members, a second structural member rotatable relative to the first structural member, and a plurality of pliable valve members connecting the first structural member with the second structural member such that rotation of the second structural member relative to the first structural member can urge the valve members between an open and a closed state. In particular, the rotation of the second structural member can be responsive to the natural flow of a biological fluid.

A conventional prosthetic valve can include a plurality of pliable valve leaflets having commissures at the intersection of two strut members. The prosthetic valve can further include a skirt material coupled to the strut members.

A particular advantage of a support structure in accordance with embodiments of the invention is that it enables a prosthetic valve to be readily retrieved and repositioned in the body. If following deployment, the valve is malpositioned or deemed dysfunctional, the support structure allows the valve to be readily repositioned and re-deployed at a new implant site, or removed from the body entirely. This feature of the device can prevent serious complications and save lives by enabling the repair of mal-positioned devices in the body.

BRIEF DESCRIPTION OF THE DRAWINGS

The foregoing and other objects, features and advantages of the invention will be apparent from the following more particular description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Particular embodiments of the invention include endoluminal support structures (stents) and prosthetic valves.

Figure 1:
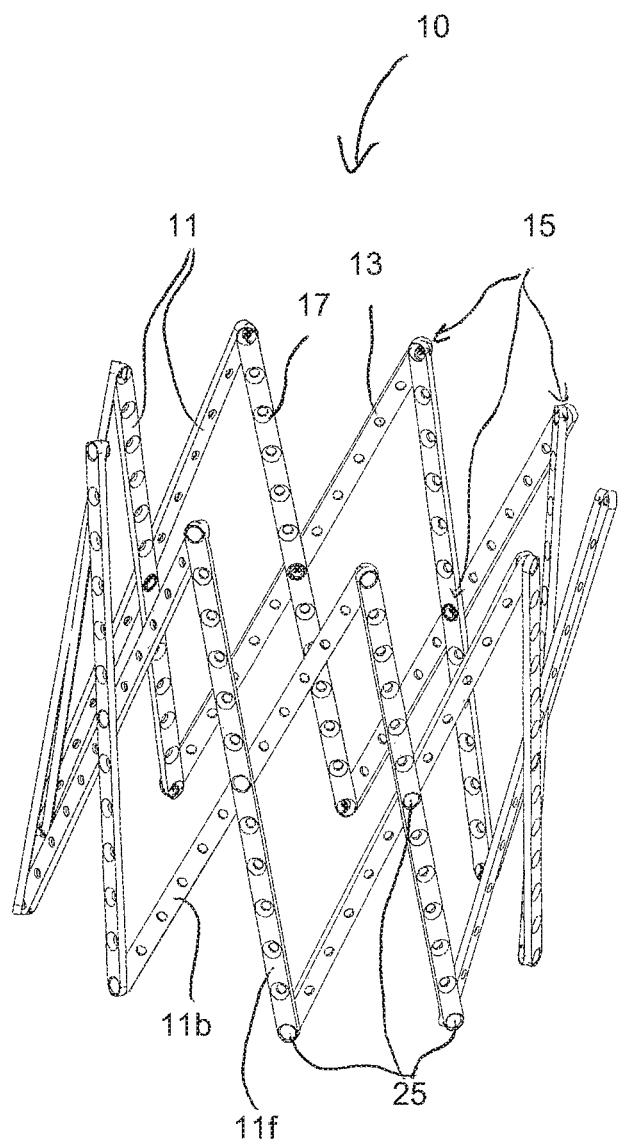
FIG. 1 is a perspective view of a particular endoluminal support structure.

FIG. 1 is a perspective view of a particular endoluminal support structure. As shown, the support structure 10 is a medical stent that includes a plurality of longitudinal strut members 11 interconnected by a plurality of swivel joints 15. In particular, the swivel joints 15 allow the interconnected strut members 11 to rotate relative to each other. As shown, there are eighteen struts 11.

The strut members 11 are fabricated from a rigid or semi-rigid biocompatible material, such as plastics or other polymers and metal alloys, including stainless steel, tantalum, titanium, nickel-titanium (e.g. Nitinol), and cobalt-chromium (e.g. ELGILOY). The dimensions of each strut can be chosen in accordance with its desired use. In a particular embodiment, each strut member is made from stainless steel, which is 0.005-0.020 inch thick. More particularly, each strut is 0.010 inch thick 300 series stainless steel. While all struts 11 are shown as being of uniform thickness, the thickness of a strut can vary across a strut, such as a gradual increase or decrease in thickness along the length of a strut. Furthermore, individual struts can differ in thickness from other individual struts in the same support structure.

As shown, each strut member 11 is bar shaped and has a front surface 11f and a back surface 11b. The strut members can however be of different geometries. For example, instead of a uniform width, the struts can vary in width along its length. Furthermore, an individual strut can have a different width than another strut in the same support structure. Similarly, the strut lengths can vary from strut to strut within the same support structure. The particular dimensions can be chosen based on the implant site.

Furthermore, the struts can be non-flat structures. In particular, the struts can include a curvature, such as in a concave or convex manner in relationship to the inner diameter of the stent structure. The struts can also be twisted. The nonflatness or flatness of the struts can be a property of the material from which they are constructed. For example, the struts can exhibit shape-memory or heat-responsive changes in shape to the struts during various states. Such states can be defined by the stent in the compressed or expanded configuration.

Furthermore, the strut members 11 can have a smooth or rough surface texture. In particular, a pitted surface can provide tensile strength to the struts. In addition, roughness or pitting can provide additional friction to help secure the support structure at the implant site and encourage irregular encapsulation of the support structure 10 by tissue growth to further stabilize the support structure 10 at the implant site over time.

In certain instances, the stent could be comprised of struts that are multiple members stacked upon one another. Within the same stent, some struts could include elongated members stacked upon one another in a multi-ply configuration, and other struts could be one-ply, composed of single-thickness members. Within a single strut, there can be areas of one-ply and multi-ply layering of the members.

Each strut member 11 also includes a plurality of orifices 13 spaced along the length of the strut member 11. On the front surface 11f, the orifices are countersunk 17 to receive the head of a fastener. In a particular embodiment, there are thirteen equally spaced orifices 13 along the length of each strut member 11, but more or less orifices can be used. The orifices 13 are shown as being of uniform diameter and uniform spacing along the strut member 11, but neither is required.

The strut members 11 are arranged as a chain of four-bar linkages. The strut members 11 are interconnected by swivelable pivot fasteners 25, such as rivets, extending through aligned orifices 13. It should be understood that other swivelable fasteners 25 can be employed such as screws, bolts, ball-in-socket structures, nails, or eyelets, and that the fasteners can be integrally formed in the struts 11 such as a peened semi-sphere interacting with an indentation or orifice, or a male-female coupling. In addition to receiving a fastener, the orifices 13 also provide an additional pathway for tissue growth-over to stabilize and encapsulate the support structure 10 over time.

Figure 2:
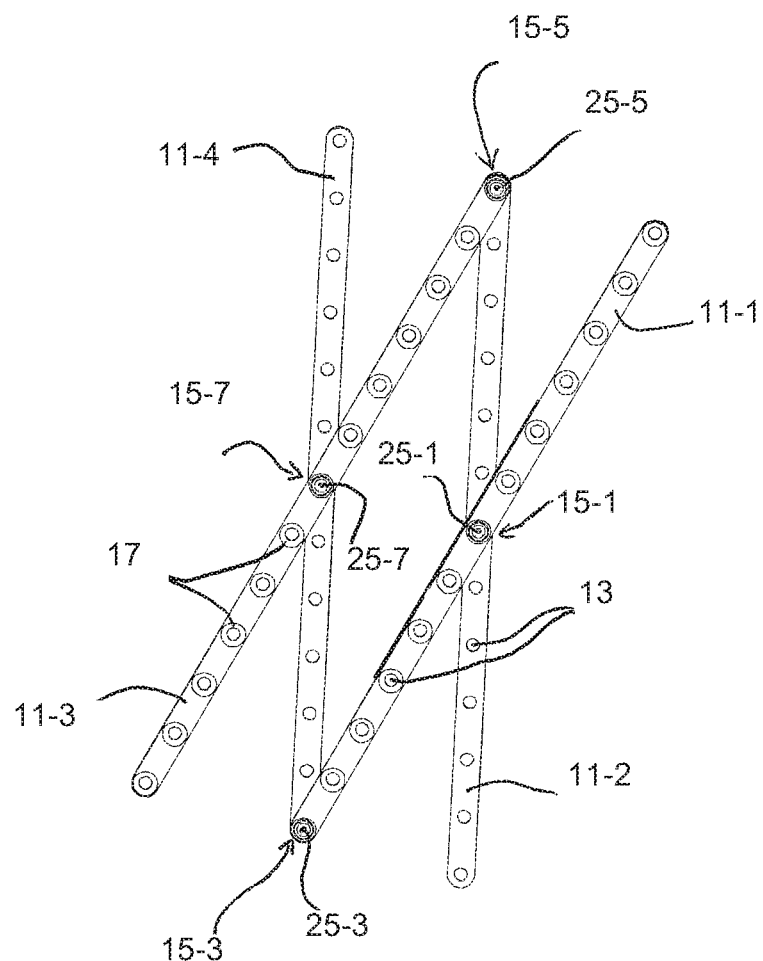
FIG. 2 is a perspective view of a four strut section of the stent of FIG. 1.

FIG. 2 is a perspective view of a four strut section of the stent of FIG. 1. As shown, two outer strut members 11-1, 11-3 overlap two inner strut members 11-2, 11-4, with their back surfaces in communication with each other.

In particular, the first strut member 11-1 is swivelably connected to the second strut member 11-1 by a middle swivel joint 15-1 using a rivet 25-1, which utilizes orifices 13 that bisect the strut members 11-1, 11-2. Similarly, the third strut member 11-3 is swivelably connected to bisect the fourth strut member 11-4 by a middle swivel joint 15-7 using a rivet 25-7. It should be understood that the middle swivel joints 15-1, 15-7 function as a scissor joint in a scissor linkage or mechanism. As shown, the resulting scissor arms are of equal length. It should also be understood that the middle joint 15-1, 15-7 need not bisect the joined strut members, but can instead utilize orifices 13 offset from the longitudinal centers of the strut members resulting in unequal scissor arm lengths.

In addition to the middle scissor joint 15-1, the first strut member 11-1 is swivelably connected to the third strut member 11-3 by a distal anchor swivel joint 15-5, located near the distal ends of the strut members 11-1, 11-3. Similarly, the first strut member 11-1 is swivelably connected to the fourth strut member 11-4 by a proximal anchor swivel joint 15-3, located near the proximal ends of the strut members 11-1, 11-4. To reduce stresses on the anchor rivets 25-3, 25-5, the distal and proximal ends of the struts 11 can be curved or twisted to provide a flush interface between the joined struts.

As can be seen, the support structure 10 (FIG. 1) is fabricated by linking together a serial chain of scissor mechanisms. The chain is then wrapped to join the last scissor mechanism with the first scissor mechanism in the chain. By actuating the linkage the links can be opened or closed, which results in expanding or compressing the stent 10 (FIG. 1).

Returning to FIG. 1, by utilizing the swivel joints 15, the diameter of the stent can be compressed for insertion through a biological lumen, such as an artery, to a selected position. The stent can then be expanded to secure the stent at the selected location within the lumen. Furthermore, after being expanded, the stent can be recompressed for removal from the body or for repositioning within the lumen.

Figure 3:
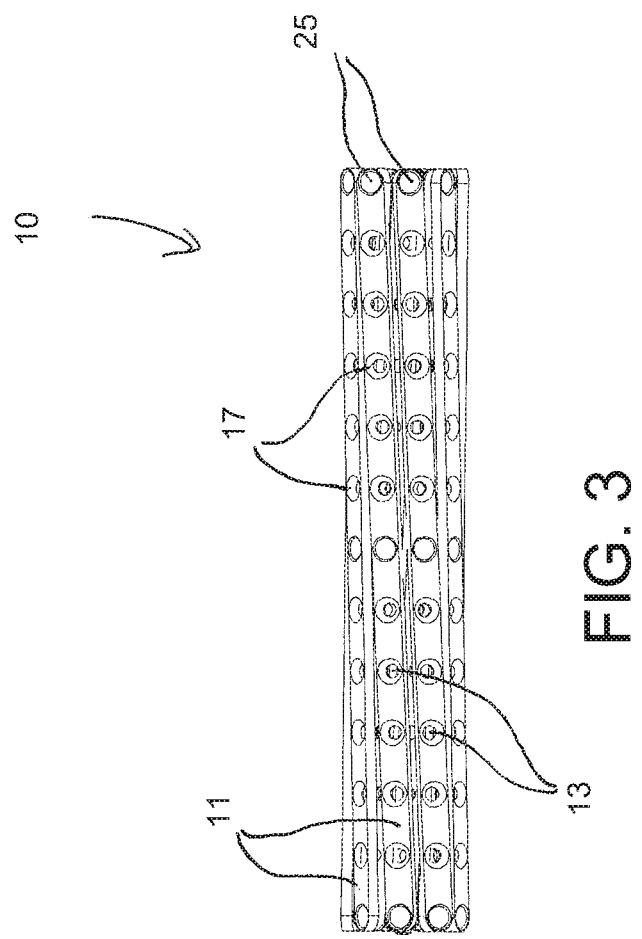
FIG. 3 is a perspective view of a compressed support structure of FIG. 1.

FIG. 3 is a perspective view of a compressed support structure of FIG. 1. When compressed, the stent 10 is at its maximum length and minimum diameter. The maximum length is limited by the length of the strut members, which in a particular embodiment is 15 mm. The minimum diameter is limited by the width of the strut members, which in a particular embodiment is 0.052 inch.

Figure 4:
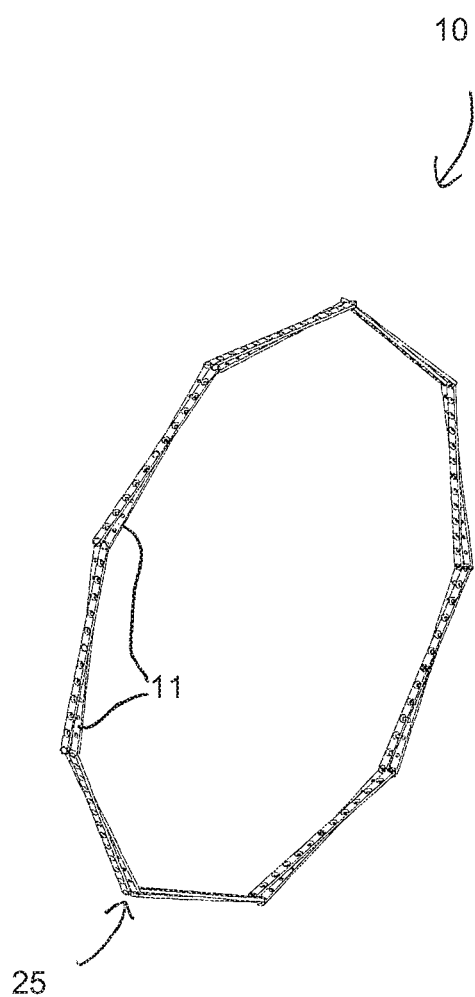
FIG. 4 is a perspective view of the support structure of FIG. 1 in a fully expanded state.

FIG. 4 is a perspective view of the support structure of FIG. 1 in a fully expanded state. As shown, the fully expanded support structure 10 forms a ring, which can be used as an annuloplasty ring. In particular, if one end of the stent circumference is attached to tissue, the compression of the stent will enable the tissue to cinch. Because the stent has the ability to have an incremental and reversible compression or expansion, the device could be used to provide an individualized cinching of the tissue to increase the competency of a heart valve. This could be a useful treatment for mitral valve diseases, such as mitral regurgitation or mitral valve prolapse.

While the support structure 10 can be implanted in a patient during an open operative procedure, a closed procedure will often be more desirable. As such, the support structure 10 can include an actuation mechanism to allow a surgeon to expand or compress the support structure from a location remote from the implant site. Due to the properties of a scissor linkage wrapped into a cylinder (FIG. 1), actuation mechanisms can exert work to expand the stent diameter by either increasing the distance between neighboring scissor joints, and decreasing the distance between the anchor joints.

Figure 18:
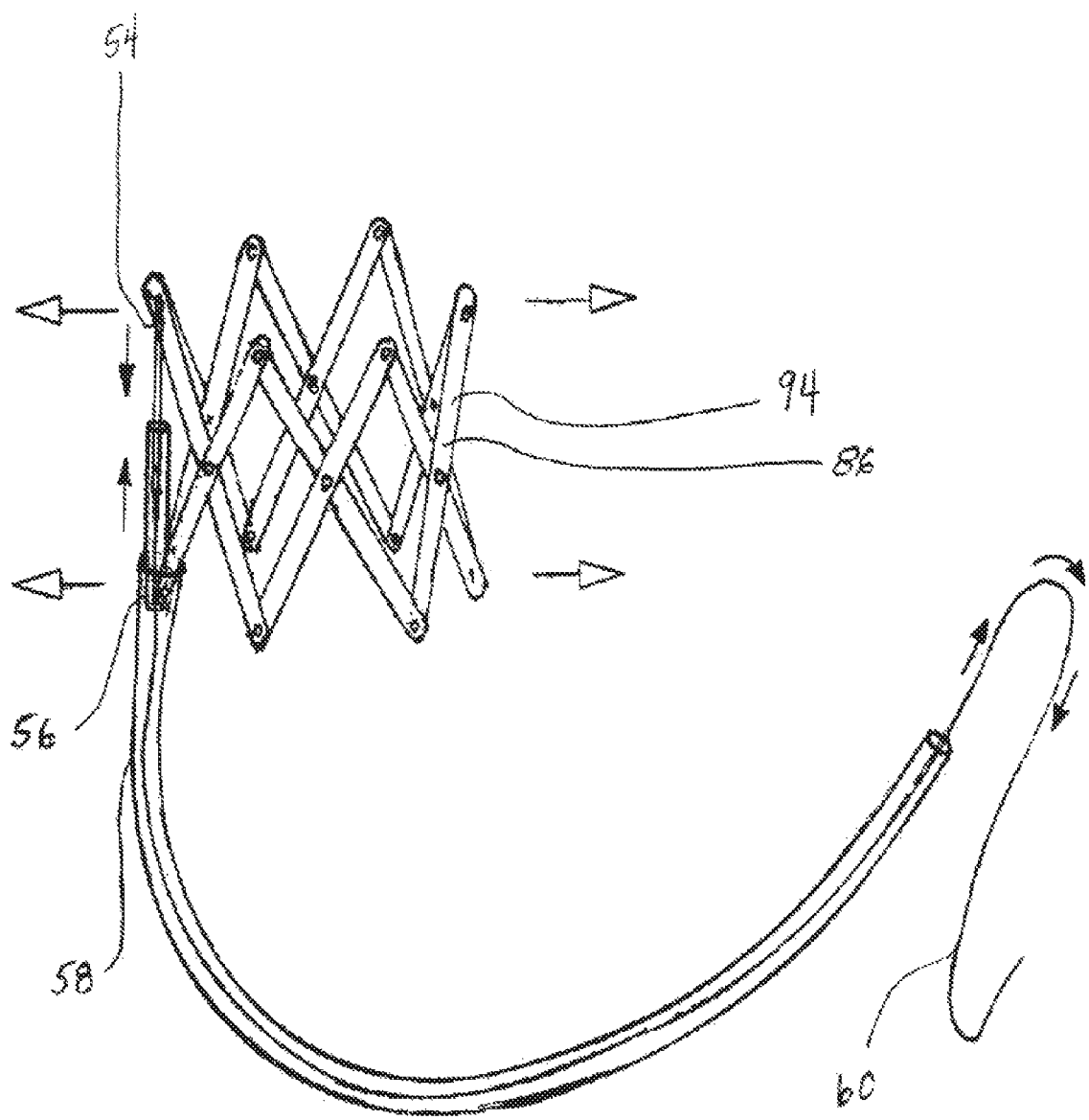
FIG. 18 is a perspective view of a support structure showing an expansion element and a mechanism.

FIG. 18 shows a mechanism and elements to expand support structure 86. In this case, an upper expansion element 54 is attached to one of the upper bar 94 of support structure 86. A lower expansion element 56 is secured to the opposing lower bar 94. In order to change the diameter of the device, upper expansion element 54 is displaced towards lower expansion element 56, by pulling on wire 60, which is attached to element 54, causing a radial expansion of the device (large arrows). The catheter 58 attached to a lower bar 94 of the support structure 86, provides a counterforce to pulling on wire 60, effectively holding the support structure 86 in a fixed position during expansion of the support structure.

The general principle of the mechanism is that applying an opposing axial load to any pair of opposing upper and lower ends of the bars 94 of the device, causes radial expansion of the device. The elements, such as 54, could be simplified further by being replaced by a simple pull wire exerting the same forces on the structure.

Figure 5:
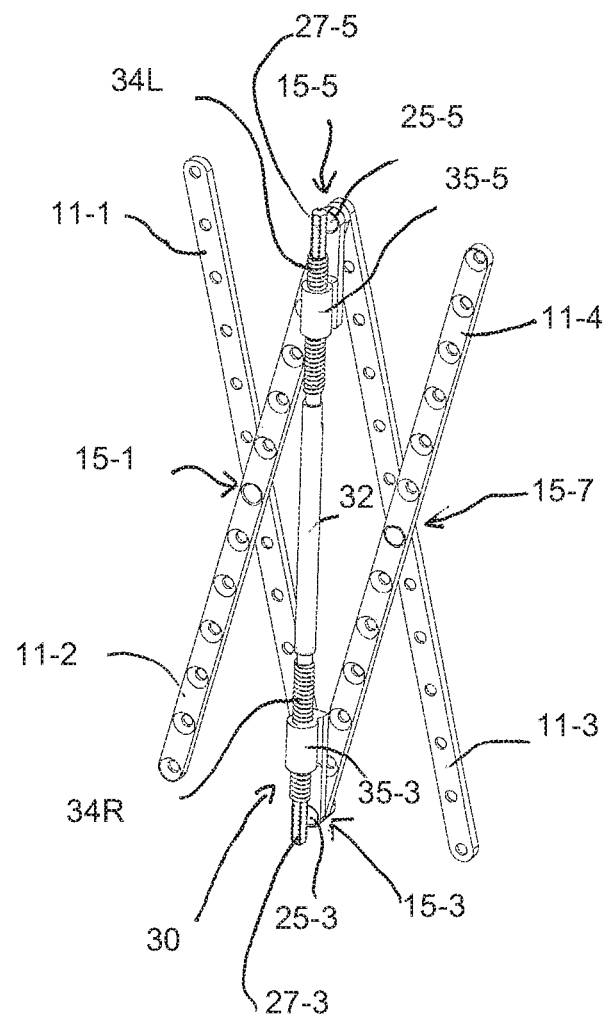
FIG. 5 is a perspective view of the support structure of FIG. 2 having a particular actuator mechanism.

FIG. 5 is a perspective view of the support structure of FIG. 2 having a particular actuator mechanism. As shown, the actuator mechanism 30 includes a dual-threaded rod 32 positioned on the inside of the support structure 10 (FIG. 1). It should be understood, however, that the actuator mechanism 30 can instead be positioned on the outside of the support structure 10. Whether positioned on the inside or outside, the actuator mechanism 30 operates in the same way. The rod includes right-hand threads 34R on its proximal end and left-hand threads 34L on its distal end. The rod 32 is mounted the anchor points 15-3, 15-5 using a pair of threaded low-profile support mounts 35-3, 35-5. Each end of the rod 32 is terminated by a hex head 37-3, 37-5 for receiving a hex driver (not shown). As should be understood, rotating the rod 32 in one direction will urge the anchor points 25-3, 25-5 outwardly to compress the linkages while rotating the rod 32 in the opposite direction will urge the anchor points 25-3, 25-5 inwardly to expand the linkages.

Figure 6:
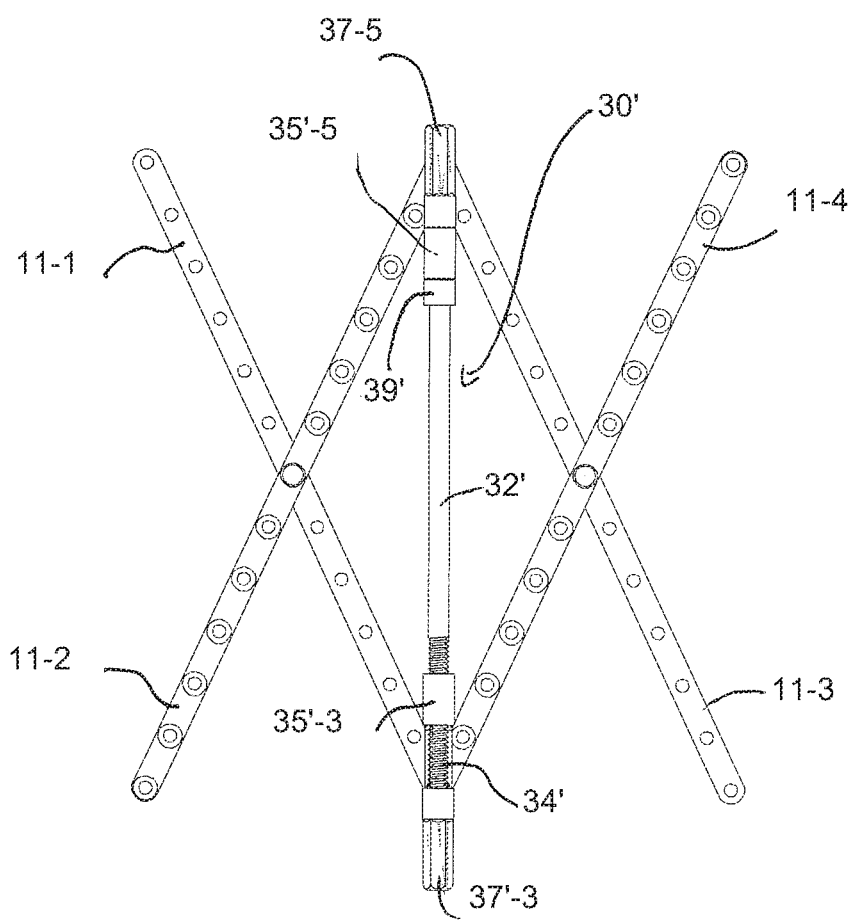
FIG. 6 is a perspective view of the support structure of FIG. 2 having another particular actuator mechanism.

FIG. 6 is a perspective view of the support structure of FIG. 2 having another particular actuator mechanism. As shown, the actuator mechanism 30' includes a single-threaded rod 32' positioned on the inside of the support structure 10 (FIG. 1). The rod 32' includes threads 34' on one of its ends. The rod 32' is mounted to low profile anchor points 15-3, 15-5 using a pair of support mounts 35'-3, 35'-5, one of which is threaded to mate with the rod threads 34'. The unthreaded end of the rod 32' includes a retaining stop 39' that bears against the support mount 35'-5 to compress the support structure. Each end of the rod 32' is terminated by a hex head 37'-3, 37'-5 for receiving a hex driver (not shown). Again, rotating the rod 32' in one direction will urge the anchor points 25-3, 25-5 outwardly to compress the linkages while rotating the rod 32' in the opposite direction will urge the anchor points 25-3, 25-5 inwardly to expand the linkages.

In addition, because the struts overlap, a ratcheting mechanism can be incorporated to be utilized during the sliding of one strut relative to the other. For example, the stent could lock at incremental diameters due to the interaction of features that are an integral part of each strut. An example of such features would be a male component (e.g. bumps) on one strut surface which mates with the female component (e.g. holes) on the surface of the neighboring strut surface, as the two struts slide pass one another. Such structures could be fabricated to have an orientation, such that they incrementally lock the stent in the expanded configuration as the stent is expanded. Such a stent could be expanded using a conventional balloon or other actuation mechanism described in this application.

Because the support structure 10 of FIGS. 5 and 6 are intended to be implanted during a closed surgical procedure, the actuator mechanism is controlled remotely by a surgeon. In a typical procedure, the support structure 10 is implanted through a body lumen, such as the femoral artery using a tethered endoluminal catheter. As such, the actuator mechanism 30 can be controlled via the catheter.

Figure 7:
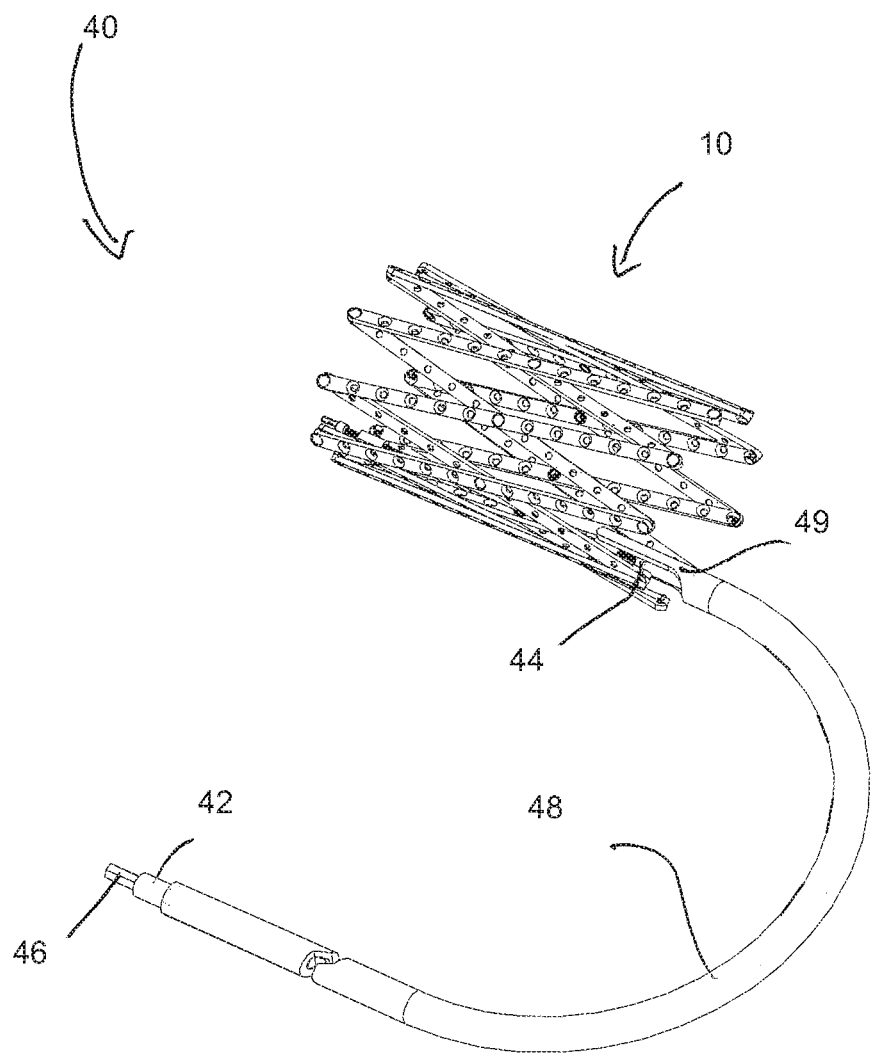
FIG. 7 is a perspective view of a particular support structure and control catheter assembly usable with the actuator mechanisms of FIGS. 5 and 6.

FIG. 7 is a perspective view of a particular support structure and control catheter assembly usable with the actuator mechanisms of FIGS. 5 and 6. The control catheter 40 is dimensioned to be inserted with the support structure through a biological lumen, such as a human artery. As shown, the control catheter 40 includes a flexible drive cable 42 having a driver 44 on its distal end that removably mates with a hex head 37, 37' of the actuator mechanism (FIGS. 5 and 6). The proximal end of the cable 42 includes a hex head 46. In operation, the proximal hex head 46 of the cable 42 is rotated by a surgeon, using a thumb wheel or other suitable manipulator (not shown). Rotation of the hex head 46 is transferred by the cable 42 to the driver head 44 to turn the actuator rod 30, 30' (FIGS. 5 and 6).

The cable 42 is encased by a flexible outer sheath 48. The distal end of the outer sheath 48 includes a lip or protuberance 49 shaped to interface with the support structure 10. When the cable 42 is turned, the outer sheath lip 49 interacts with the support structure 10 to counteract the resulting torque.

By employing threads, the rod is self-locking to maintain the support structure in the desired diameter. In a particular embodiment, the rod 32, 32' has a diameter of 1.0 mm and a thread count of 240 turns/inch. While a threaded rod and drive mechanism are described, other techniques can be employed to actuate the linkages depending on the particular surgical application. For example, the actuator mechanism can be disposed within the thickness of the strut members, instead of inside or outside of the stent. For example, worm gears or a rack and pinion mechanism can be employed as known in the art. One of ordinary skill in the art should recognize other endoluminal actuation techniques. In other situations, the support structure can be implanted during an open procedure, which may not require an external actuation mechanism.

Although there are other uses for the described support structure, such as drug delivery, a particular embodiment supports a prosthetic valve. In particular, the support structure is used in combination with a prosthetic valve, such as for an aortic valve replacement.

Figure 19:
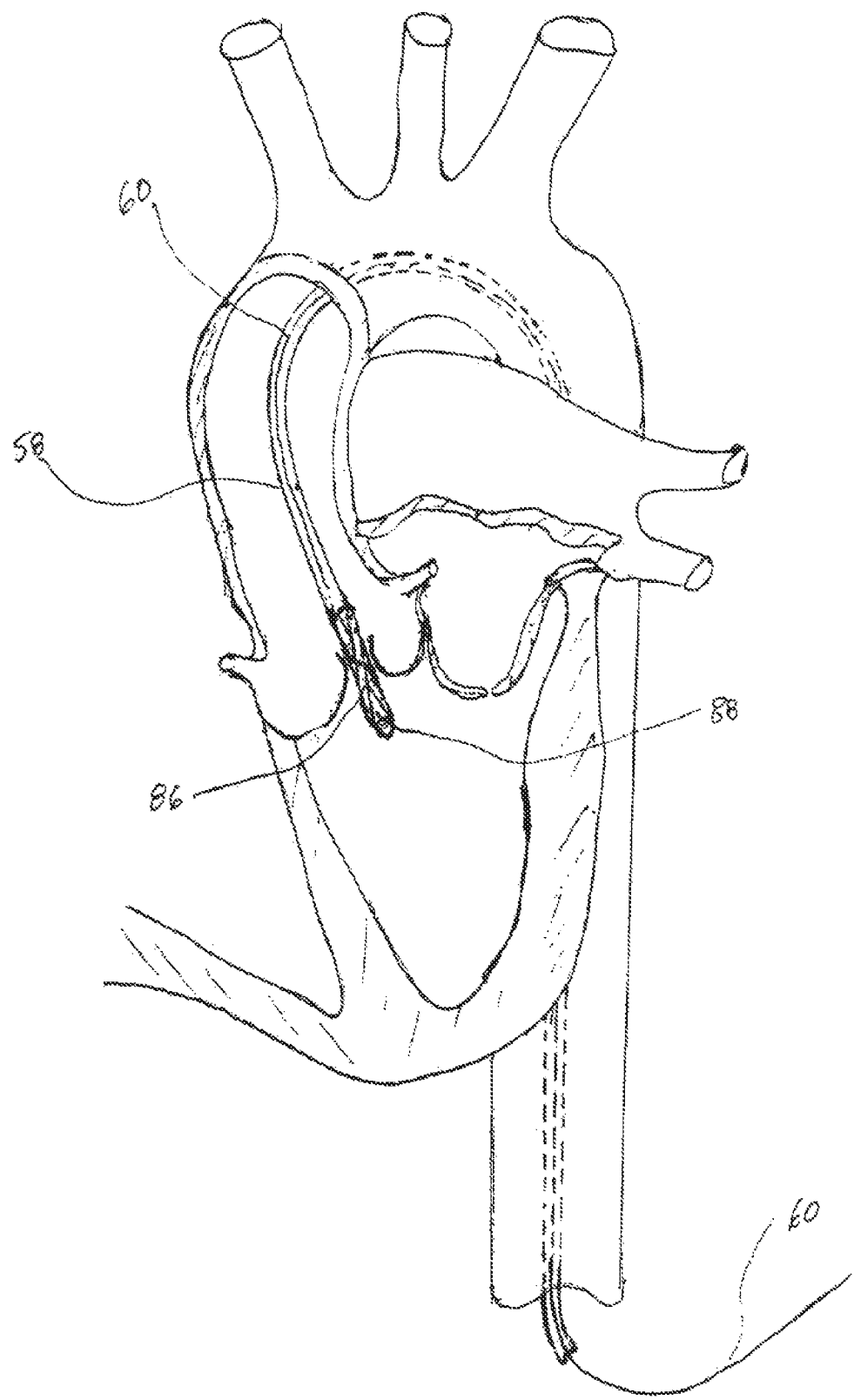
FIG. 19 is a cross-sectional view of a heart, showing the catheter deployment of a valve and a support structure as an aortic valve replacement, using the retrograde approach.

FIG. 19 depicts the retrograde delivery of the device as an aortic valve replacement in a cross-sectional view of the heart. The valve 88 is compressed in the support structure 86. A catheter 58 is used to pass the valve 88 and support structure 86 into the femoral artery at the groin. The catheter is advanced to the aortic valve site under fluoroscopic guidance. The support structure is deployed at the site by pulling on the expansion wire 60 as shown in FIG. 18.

Proper positioning of the valve 88 and support structure 86 at the implant site is confirmed by observing the valve function under fluoroscopy and the stabilization of hemodynamic parameters. After proper valve position is confirmed, the catheter 58 and all wires are detached from the device and removed from the body. The device could be delivered to the mitral position using the retrograde approach.

Figure 20:
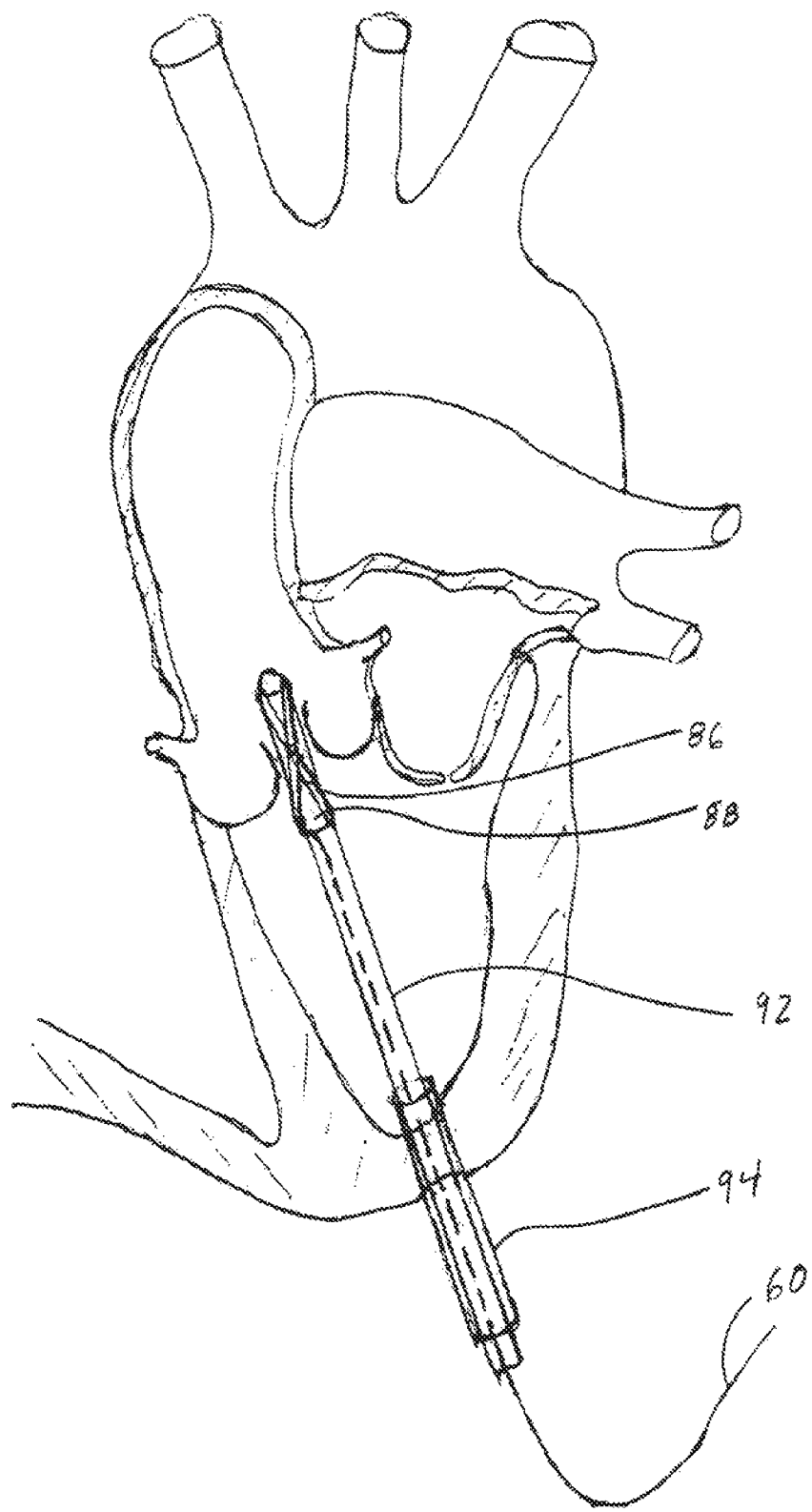
FIG. 20 is a cross-sectional view of a heart, showing the catheter deployment of a valve and a support structure as an aortic valve replacement, using the apical approach.

FIG. 20 depicts a cross-sectional view of the heart showing the apical delivery of the device for aortic valve replacement. A small incision is made in the chest wall, and a cannula 80 is inserted in the left ventricle through the apex of the heart. Valve 88 and support structure 86, on catheter 92, is passed through cannula 80. Following confirmation of correct valve position by fluoroscopy, a wire 60 is pulled to expand the device. The apical approach could be used for deployment of the valve into the mitral position.

Figure 21:
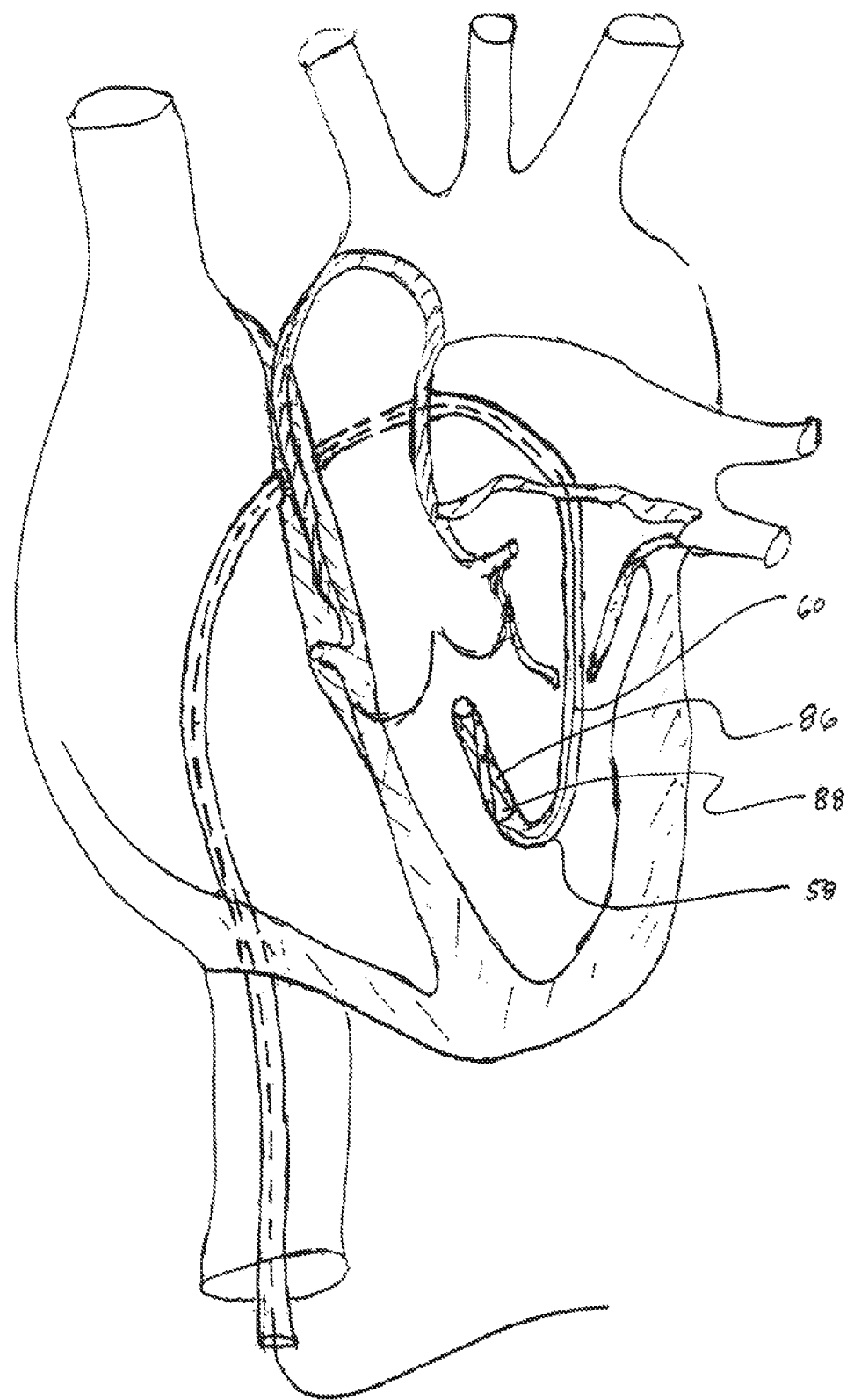
FIG. 21 is a cross-sectional view of a heart, showing the catheter deployment of a valve and a support structure as an aortic valve replacement, using the antegrade approach.

FIG. 21 depicts antegrade delivery of the device for aortic or mitral valve replacement using a close chest procedure. The valve 88 and support structure 86 mounted on a catheter 56 is inserted into femoral vein at the groin and advanced in the inferior vena cava and into right atrium. Under fluoroscopic guidance, the catheter is advanced across the septum and into the left atrium. The device is deployed at the implant site by pulling on wire 60.

Figure 8:
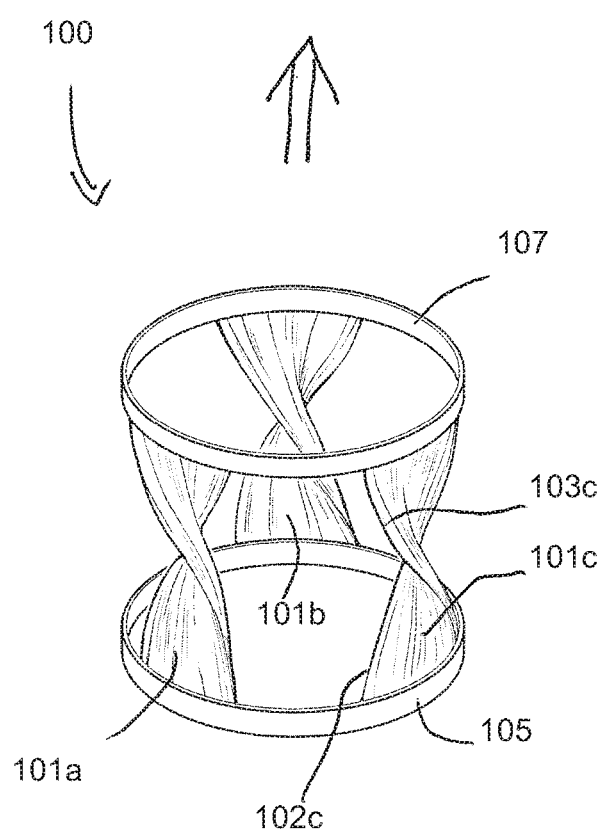
FIG. 8 is a perspective view of a particular rotating prosthetic valve assembly.

FIG. 8 is a perspective view of a particular rotating prosthetic valve assembly. The prosthetic valve 100 comprises a three leaflet configuration shown in an open position. The leaflets are derived from a biocompatible material, such as animal pericardium (e.g. bovine, porcine, equine), human pericardium, chemically treated pericardium, gluteraldehyde-treated pericardium, tissue engineered materials, a scaffold for tissue engineered materials, autologous pericardium, cadaveric pericardium, Nitinol, polymers, plastics, PTFE, or any other material known in the art.

The leaflets 101a, 101b, 101c are attached to a stationary cylindrical member 105 and a non-stationary cylindrical member 107. One side of each leaflet 101 is attached to the non-stationary cylindrical member 107. The opposing side of each leaflet 101 is attached to the stationary cylindrical member 105. The attachment of each leaflet 101 is in a direction generally perpendicular to the longitudinal axis of the cylindrical members 105, 107. In this embodiment, each leaflet 101 is pliable, generally rectangular in shape, and has a 180 degree twist between its attachments to stationary member 105 and non-stationary member 107. Each leaflet 101 has an inner edge 102 and an outer edge 103, with the edges 102c, 103c of one leaflet 101c being referenced in the figure. As known in the art, the leaflets can be fabricated from either biological or non-biological materials, or a combination of both.

One way to actuate the valve to close is by utilizing the forces exerted by the normal blood flow or pressure changes of the cardiac cycle. More specifically, the heart ejects blood through the fully open valve in the direction of the arrow shown in FIG. 8. Shortly thereafter, the distal or downstream blood pressure starts to rise relative to the proximal pressure across the valve, creating a backpressure on the valve.

Figure 9:
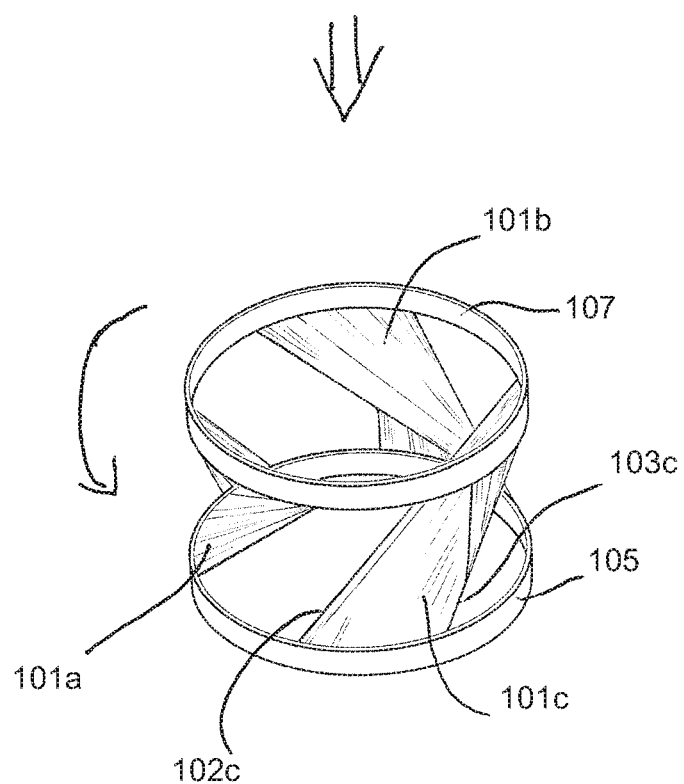
FIG. 9 is a perspective view of the valve assembly of FIG. 8 while being closed.

FIG. 9 is a perspective view of the valve assembly of FIG. 8 while being closed. That backpressure along the direction of the arrow causes the axially displacement of the leaflets 101 and non-stationary member 107 towards the stationary cylindrical member 105. As the leaflets 101 move from a vertical to horizontal plane relative to the longitudinal axis, a net counter-clockwise torque force is exerted on the non-stationary member 107 and leaflets 101. The torque force exerts a centripetal force on the leaflets 101.

Figure 10:
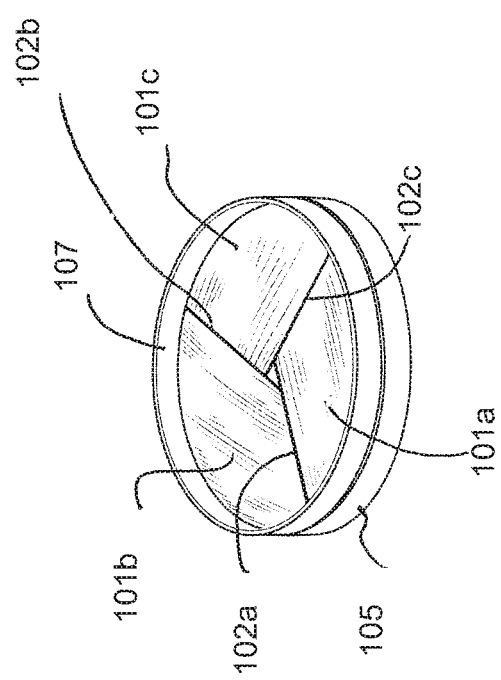
FIG. 10 is a perspective view of the valve assembly of FIG. 8 once completely closed.

FIG. 10 is a perspective view of the valve assembly of FIG. 8 once completely closed. Complete closure of the valve 100 occurs as the leaflets 101 displace to the center of the valve and the non-stationary cylindrical member 107 rests upon the stationary member 105, as shown.

The function of the valve 100 opening can be understood by observing the reverse of the steps of valve closing, namely following the sequence of drawings from FIG. 10 to FIG. 8.

In considering the valve 100 as an aortic valve replacement, it would remain closed as shown in FIG. 10, until the heart enters systole. During systole, as the myocardium forcefully contracts, the blood pressure exerted on the valve's proximal side (the side closest to the heart) is greater than the pressure on the distal side (downstream) of the closed valve. This pressure gradient causes the leaflets 101 and non-stationary cylindrical member 107 to displace away from the stationary member 105 along the axial plane. The valve 100 briefly assumes the half-closed transition state shown in FIG. 9.

As the leaflets 101 elongate from a horizontal to vertical orientation along the axial plane, a net torque force is exerted on the leaflets 101 and non-stationary cylindrical member 107. Since the valve 100 is opening, as opposed to closing, the torque force exerted to open the valve is opposite to that exerted to close the valve. Given the configuration of embodiment shown in FIG. 9, the torque force that opens the valve would be in clockwise direction.

The torque forces cause the leaflets 101 to rotate with the non-stationary member 107 around the longitudinal axis of the valve 100. This, in turn, exerts a centrifugal force on each leaflet 101. The leaflets 101 undergo radial displacement away from the center, effectively opening the valve and allowing blood to flow away from the heart, in the direction shown by the arrow in FIG. 8.

To summarize, the valve passively functions to provide unidirectional blood flow by linking three forces. Axial, torque, and radial forces are translated in a sequential and reversible manner, while encoding the directionality of prior motions. First, the axial force of blood flow and pressure causes the displacement of the leaflets 101 and non-stationary members 107 relative to the stationary member 105 along the axial plane. This is translated into a rotational force on the leaflets 101 and non-stationary member 107. The torque force, in turn, displaces the leaflets 101 towards or away from the center of the valve, along the radial plane, which closes or opens the valve 100. The valve 100 passively follows the pathway of opening or closing, depending on the direction of the axial force initially applied to the valve by the cardiac cycle.

In the body, the stationary cylindrical member 105 can secured and fixed in position at the implant site, while the non-stationary member 107 and distal ends of leaflets 101 are free to displace along the axial plane. In using the prosthetic valve as an aortic valve replacement, the stationary member 105 would be secured in the aortic root. As the blood pressure or flow from the heart, increases, the valve 100 changes from its closed configuration to the open configuration, with blood ejecting through the valve 100.

Specific advantages of the rotating valve of FIGS. 8-10, along with further embodiments, are described in the above-incorporated parent provisional patent application.

Figure 11:
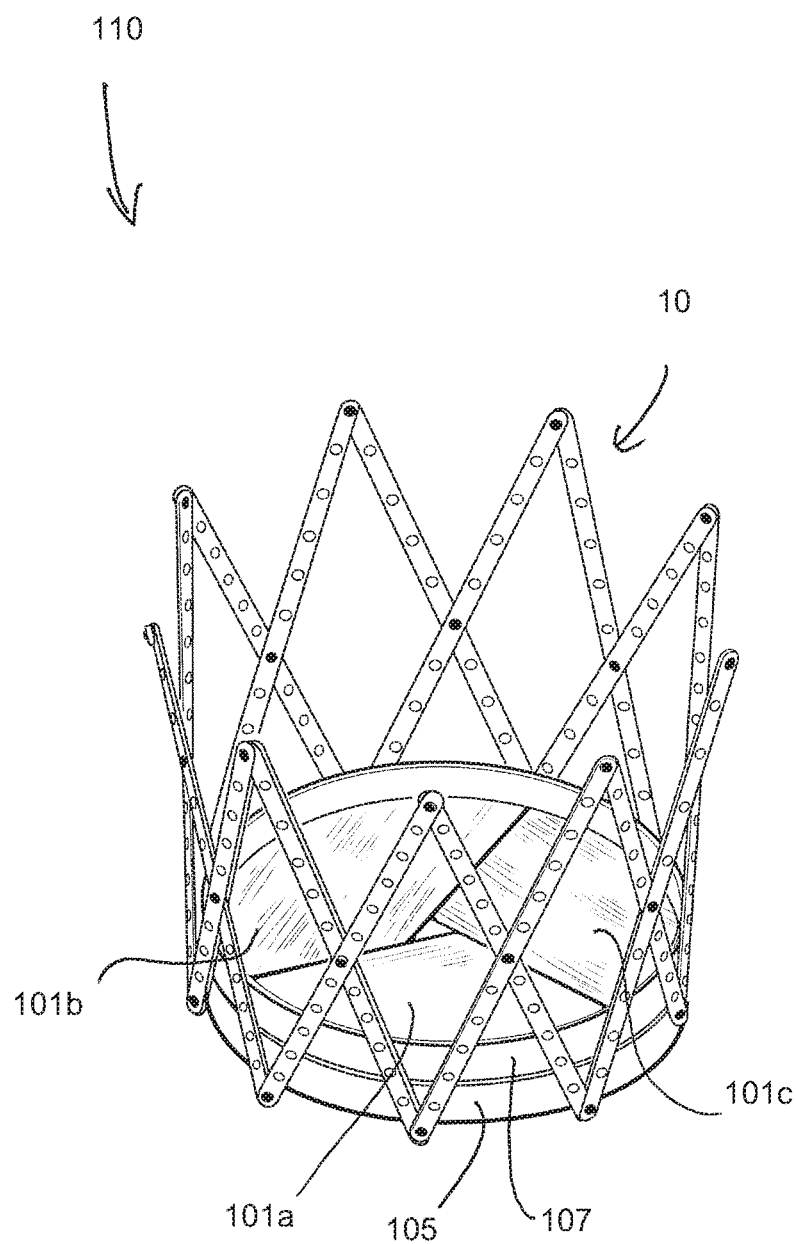
FIG. 11 is a perspective view of the valve of FIGS. 8-10 in combination with the support structure of FIG. 1.

FIG. 11 is a perspective view of the valve of FIGS. 8-10 in combination with the support structure of FIG. 1. As shown in the closed position, the valve's stationary member 105 is attached to the support structure 10. The valve's nonstationary member 107 is not attached to the support structure 10. This enables the non-stationary member 107 to displace along the axial plane along with the leaflets 101 during valve opening or closing. In this particular embodiment, the valve 100 occupies a position that is closer to one end of the support structure 10, as shown.

Figure 12:
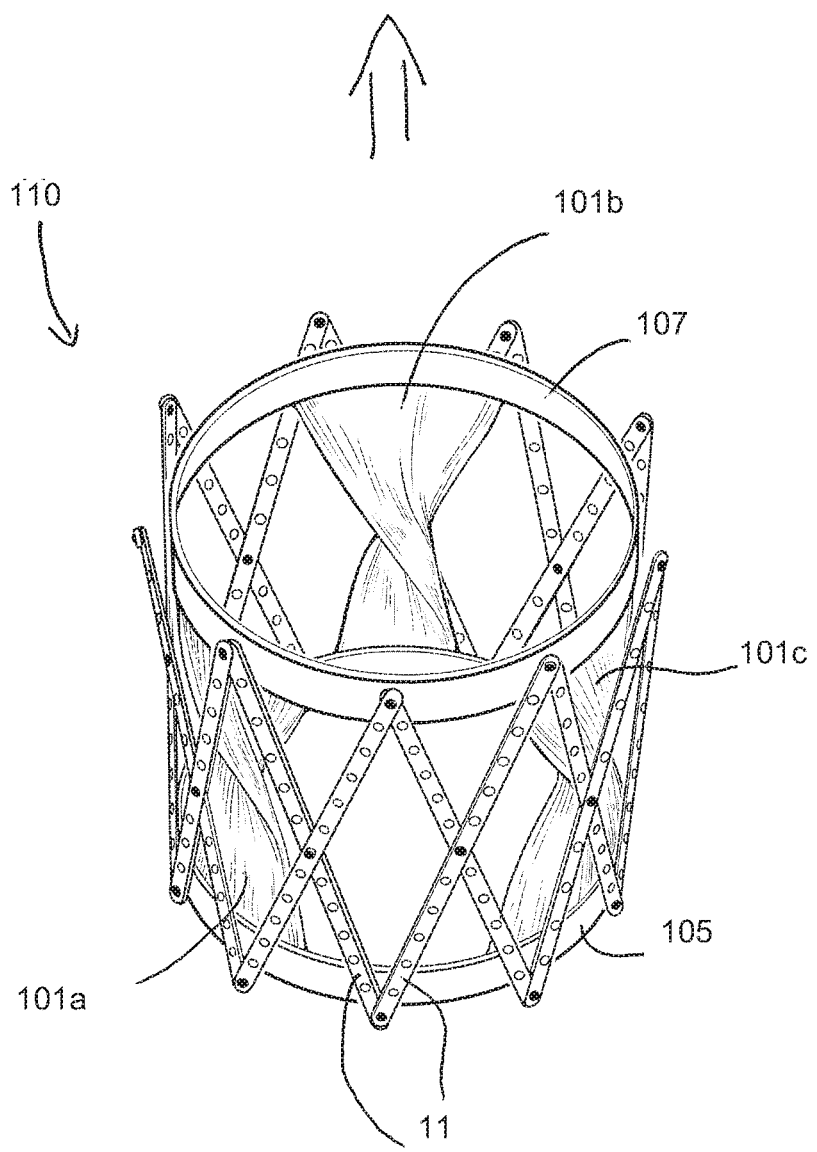
FIG. 12 is a perspective view of the valve of FIG. 11 in the open position.

FIG. 12 is a perspective view of the valve of FIG. 11 in the open position. As noted above, the non-stationary member 107 is not attached to support structure 10, and is thus free to displace along the axial plane, along with the leaflets 101. In this particular embodiment, during full opening, non-stationary member 107 and the leaflets 101 remain within the confines of the support structure 10.

The stented valve 110 can be implanted during a closed procedure as described above. However, because of the operation of the non-stationary member within the body of the stent, the actuator mechanism to compress and expand the stent would not be disposed within the stent.

Further embodiments of the stented valve 110, positioning of the valve in the body, and procedures for implantation are described in the above-incorporated parent provisional patent application. In addition, a tissue valve can be draped on the support structure. Additional embodiments should be apparent to those of ordinary skill in the art.

Figure 13:
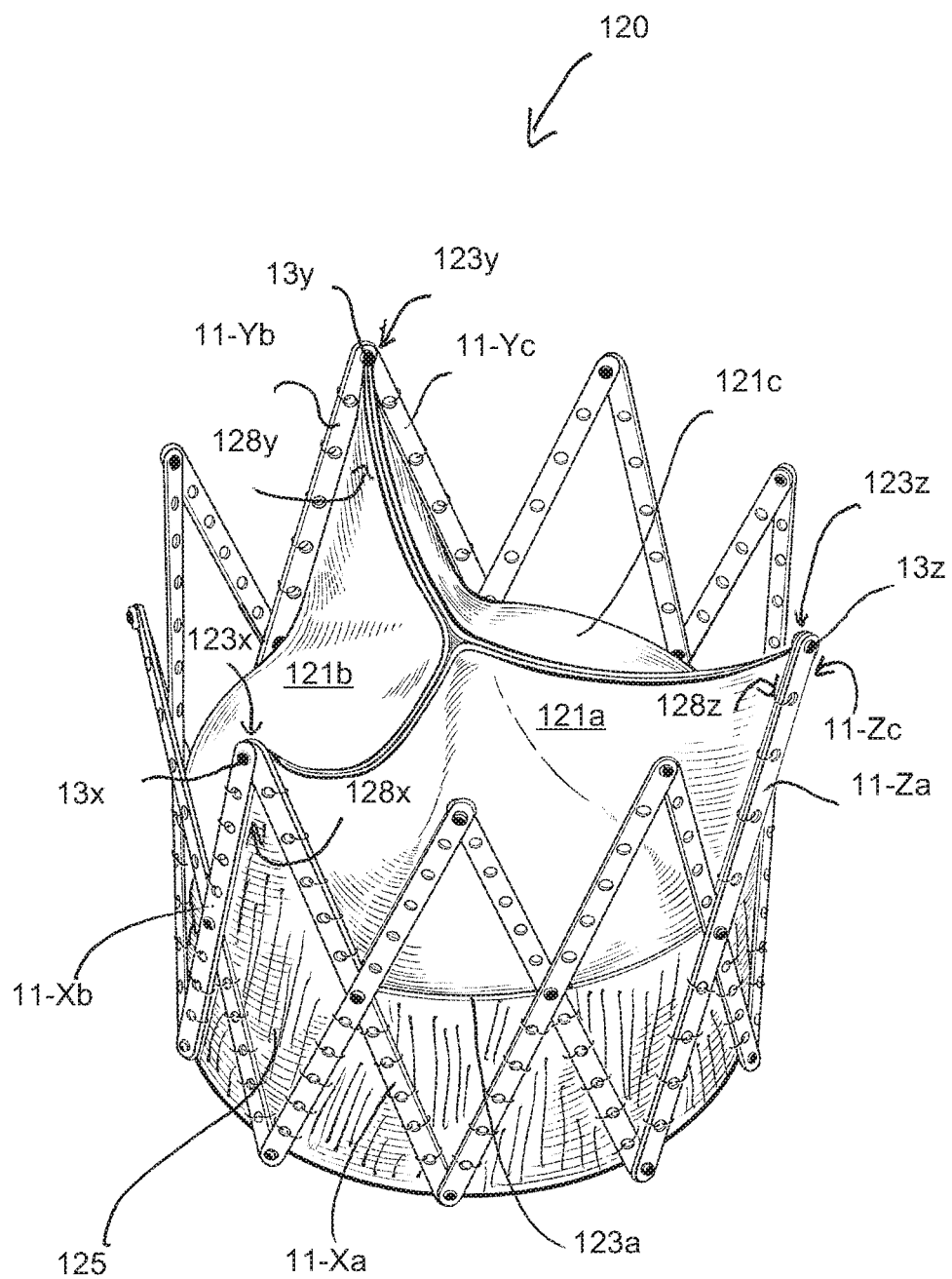
FIG. 13 is a perspective view of a traditional tissue valve mounted to the support structure of FIG. 1.

FIG. 13 is a perspective view of a traditional tissue valve mounted to the support structure of FIG. 1. As shown, a stented valve 120 includes a prosthetic tissue valve 121 attached to a support structure 10, such as that described above.

The tissue valve 121 includes three pliable semi-circular leaflets 121a, 121b, 121c, which can be derived from biocompatible materials as noted with reference to FIG. 8. Adjacent leaflets are attached in pairs to commissures 123x, 123y, 123z on the support structure 10. In particular, the commissures 123x, 123y, 123z correspond with spaced-apart distal anchor points 13x, 13y, 13z on the support structure 10. In an 18-strut stent, the commissures are attached the structure 10 via corresponding fasteners 25 at every third distal anchor point.

From the commissures, the leaflet sides are connected to the adjacent diagonal struts. That is, the sides of the first leaflet 121a are sutured to the struts 11-Xa and 11-Za, respectively; the sides of the second leaflet 121b are sutured to the struts 11-Xb and 11-Yb, respectively; and the sides of the third leaflet 121c are sutured to the struts 11-Yc and 11-Zc, respectively. Those sutures end at the scissor pivot points on the diagonal struts.

In the configuration shown, neighboring struts 11 are attached to one another in a manner that creates multiple arches 128 at the ends of the stent. Posts for leaflet attachment, or commissures, are formed by attaching neighboring leaflet to each of the struts that define a suitable arch 128x, 128y, 128z. In the configuration shown, there are three leaflets 121a, 121b, 121c, each of which is attached to a strut along two of its opposing borders. The commissures are formed by three equi-distance arches 128x, 128y, 128z in the stent.

The angled orientation of a strut in relationship to its neighboring strut enables the leaflets 121a, 121b, 121c to be attached to the stent in an triangular configuration. This triangular configuration simulates the angled attachment of the native aortic leaflet. In the native valve this creates an anatomical structure between leaflets, known as the inter-leaflet trigone. Because the anatomical inter-leaflet trigone is believed to offer structural integrity and durability to the native aortic leaflets in humans, it is advantageous to simulate this structure in a prosthetic valve.

One method of attachment of the leaflets to the struts is to sandwich the leaflet between a mutli-ply strut. The multiple layers are then held together by sutures. Sandwiching the leaflets between the struts helps to dissipate the forces on leaflets and prevent the tearing of sutures through the leaflets.

The remaining side of each leaflet 121a, 121b, 121c is sutured annularly across the intermediate strut members as shown by a leaflet seam. The remaining open spaces between the struts are draped by a biocompatible skirt 125 to help seal the valve against the implant site and thus limit paravalvular leakage. As shown, the skirt 125 is shaped to cover those portions of the stent below and between the valve leaflets.

In more detail, the skirt 125 at the base of the valve is a thin layer of material that lines the stent wall. The skirt material can be pericardial tissue, polyester, PTFE, or other material or combinations of materials suitable for accepting tissue in growth, including chemically treated materials to promote tissue growth or inhibit infection. The skirt layer functions to reduce or eliminate leakage around the valve, or "paravalvular leak". To that end, there are a number of ways to attach the skirt material layer to the stent, including:

- the skirt layer can be on the inside or the outside of the stent;
- the skirt layer can occupy the lower portion of the stent;
- the skirt layer can occupy the lower and upper portion of the stent;
- the skirt layer can occupy only the upper portion of the stent;
- the skirt layer can occupy the area between the struts that define the commissure posts;
- the skirt layer can be continuous with the leaflet material;
- the skirt layer can be sutured to the struts or a multitude of sites; or
- the skirt layer can be secured to the lower portion of the stent, and pulled or pushed up to cover the outside of the stent during the deployment in the body.

The above list is not necessarily limiting as those of ordinary skill in the art may recognize alternative draping techniques for specific applications.

Figure 14:
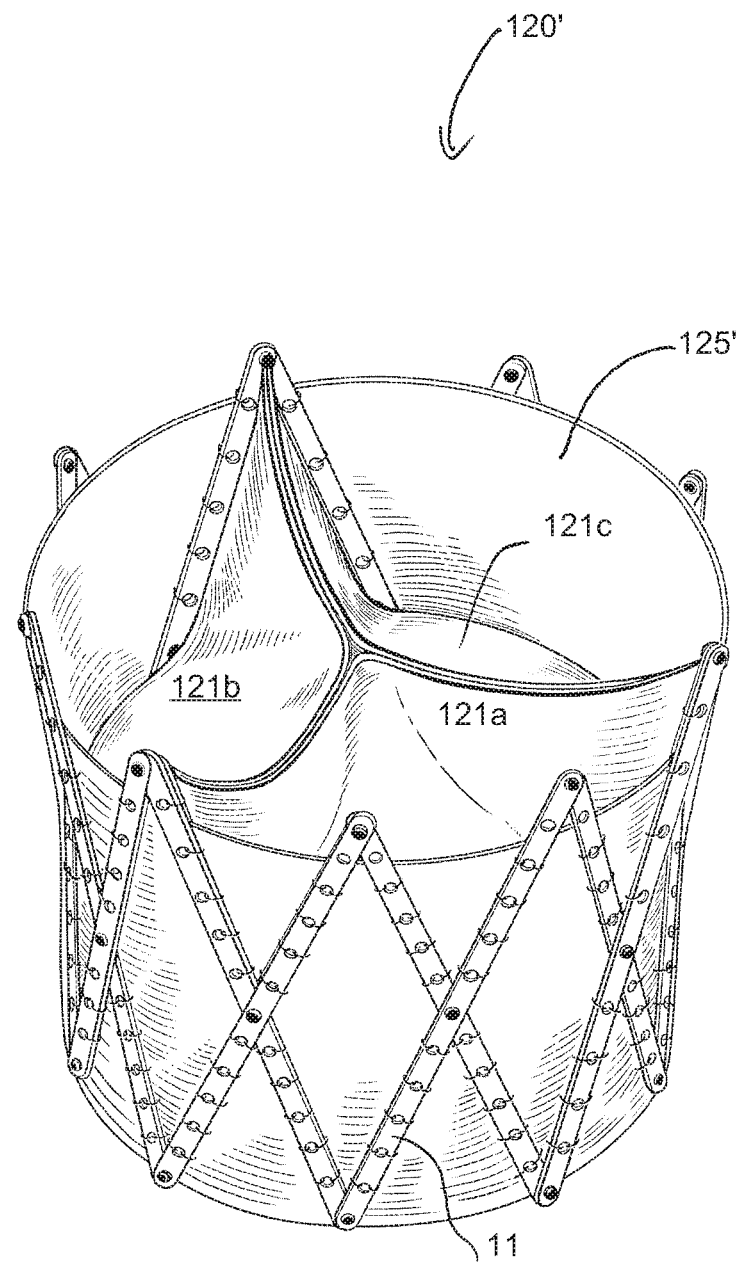
FIG. 14 is a perspective view of the valve structure of FIG. 13 having a full inner skirt.

FIG. 14 is a perspective view of the valve structure of FIG. 13 having a full inner skirt. A stented valve 120' includes a prosthetic tissue valve 121' having three leaflets 121a', 121b', 121c' attached to a support structure 10. A skirt layer 125' covers the interior surface of the stent 10. As such, the valve leaflets 121a', 121b', 121c' are sutured to the skirt layer 125'.

Figure 15:
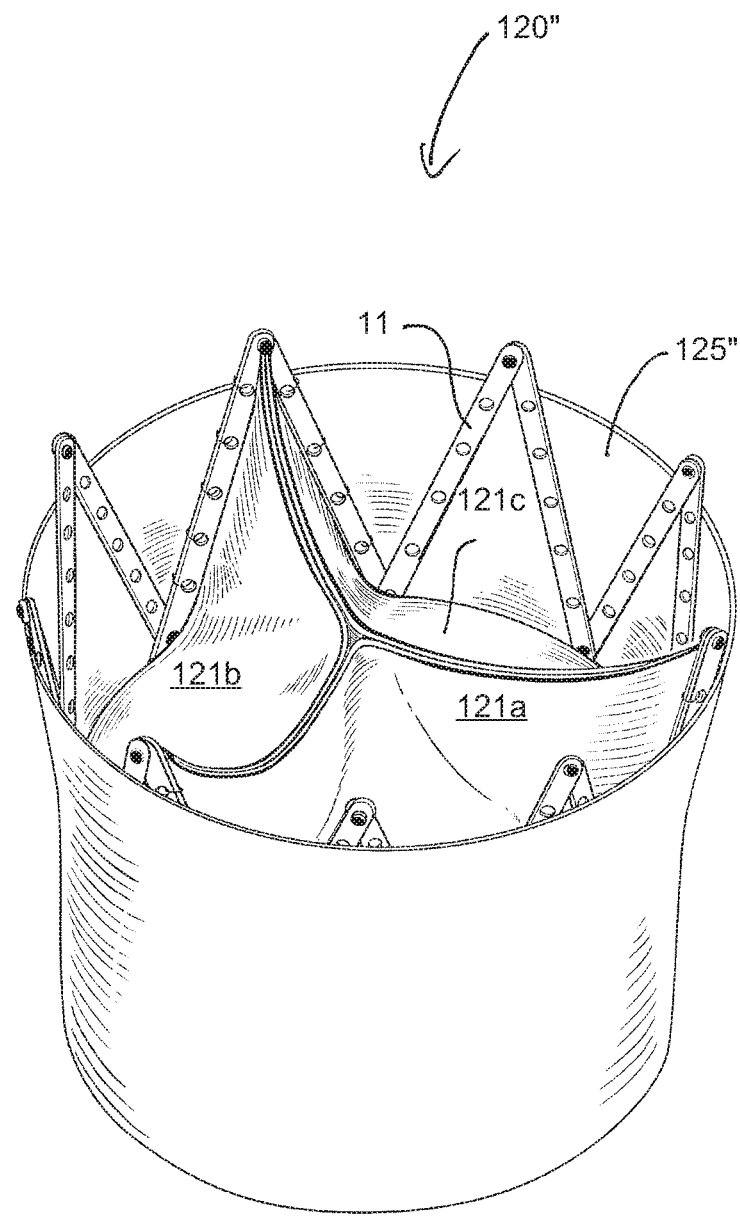
FIG. 15 is a perspective view of the valve structure of FIG. 13 having a full outer skirt.

FIG. 15 is a perspective view of the valve structure of FIG. 13 having a full outer skirt. A stented valve 120" includes a prosthetic tissue valve 121" having three leaflets 121a", 121b", 121c" attached to a support structure 10, such as that described in FIG. 13. A skirt layer 125" covers the exterior surface of the stent 10.

The tissue valve structures 120, 120', 120" can also be implanted during a closed procedure as described above. However, the actuator mechanism to compress and expand the stent would be attached to avoid the commissure points and limit damage to the skirt layer 125, 125', 125", such as by mounting the actuator mechanism on the outer surface of the stent 10.

While the above-described embodiments have featured a support structure having linear strut bars and equal length scissor arms, other geometries can be employed. The resulting shape will be other than cylindrical and can have better performance in certain applications.

Figure 16:
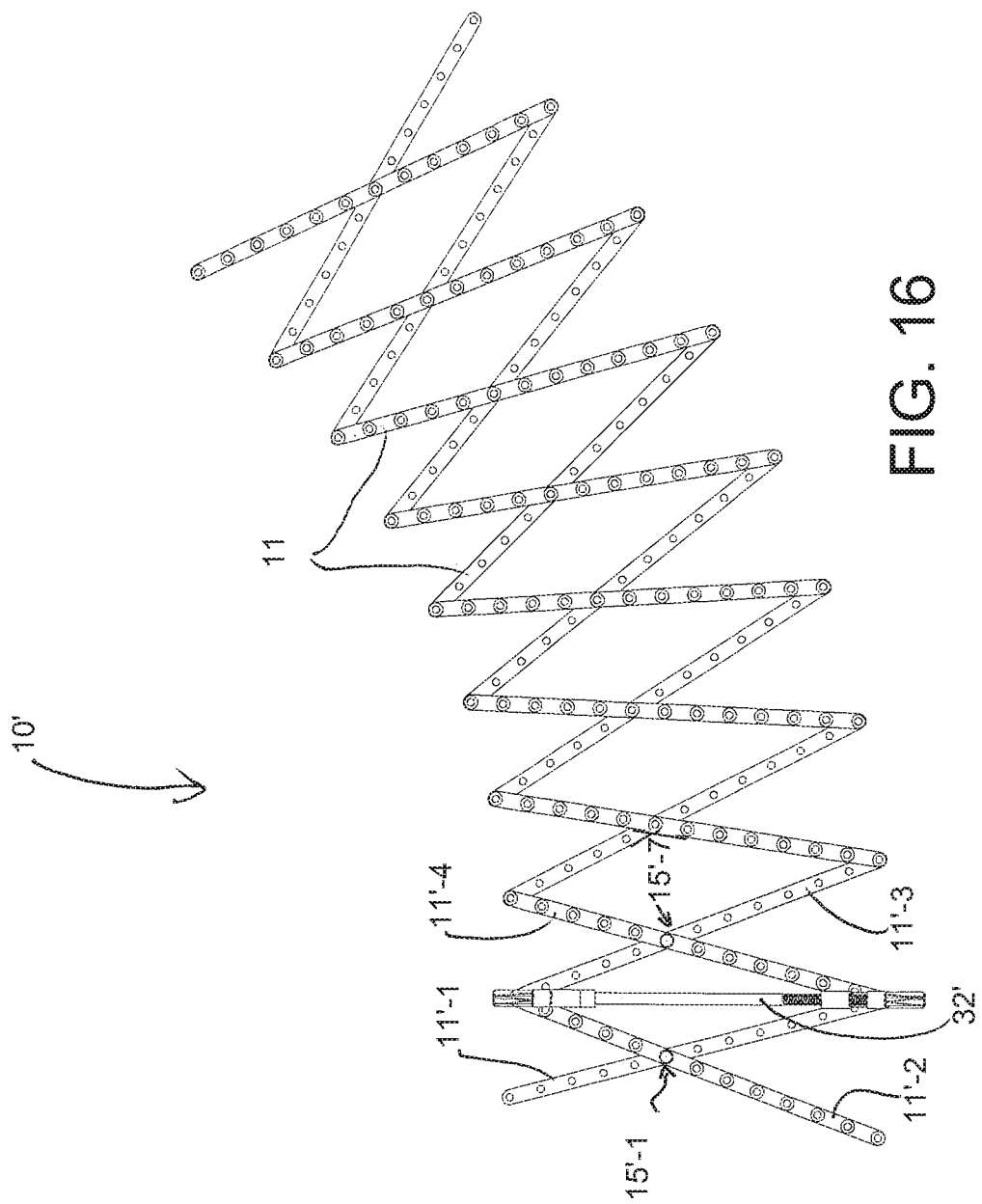
FIG. 16 is a perspective view of the arrangement of strut members in a conical-shaped support structure configuration.

FIG. 16 is a perspective view of the arrangement of strut members in a conical-shaped support structure configuration. In the conical structure 10', the strut members 11 are arranged as shown in FIG. 2, except that the middle scissor pivots do not bisect the struts. In particular, the middle scissor pivots (e.g. 15'-1, 15'-7) divide the joined strut members (e.g. 11'-1, 11'-2 and 11'-3, 11'4) into unequal segments of 5/12 and 7/12 lengths. When fully assembled, the resulting support structure thus conforms to a conical shape when expanded. For illustration purposes, the stent 10' is shown with a single-threaded actuator rod 32' (FIG. 6), but it is not a required element for this stent embodiment.

The stent 10' can also assume a cone shape in its expanded configuration by imposing a convex or concave curvature to the individual strut members 11 that comprise the stent 10'. This could be achieved by using a material with memory, such as shape-memory or temperature sensitive Nitinol.

A valve can be orientated in the cone-shaped stent 10' such that the base of the valve was either in the narrower portion of the cone-shaped stent, with the nonbase portion of the valve in the wider portion of the cone. Alternatively, the base of the valve can be located in the widest portion of the stent with the non-base portion of the valve in the less-wide portion of the stent.

The orientation of a cone-shaped stent 10' in the body can be either towards or away from the stream of blood flow. In other body lumens (e.g. respiratory tract or gastrointestinal tract), the stent could be orientated in either direction, in relationship to the axial plane.

Figure 17:
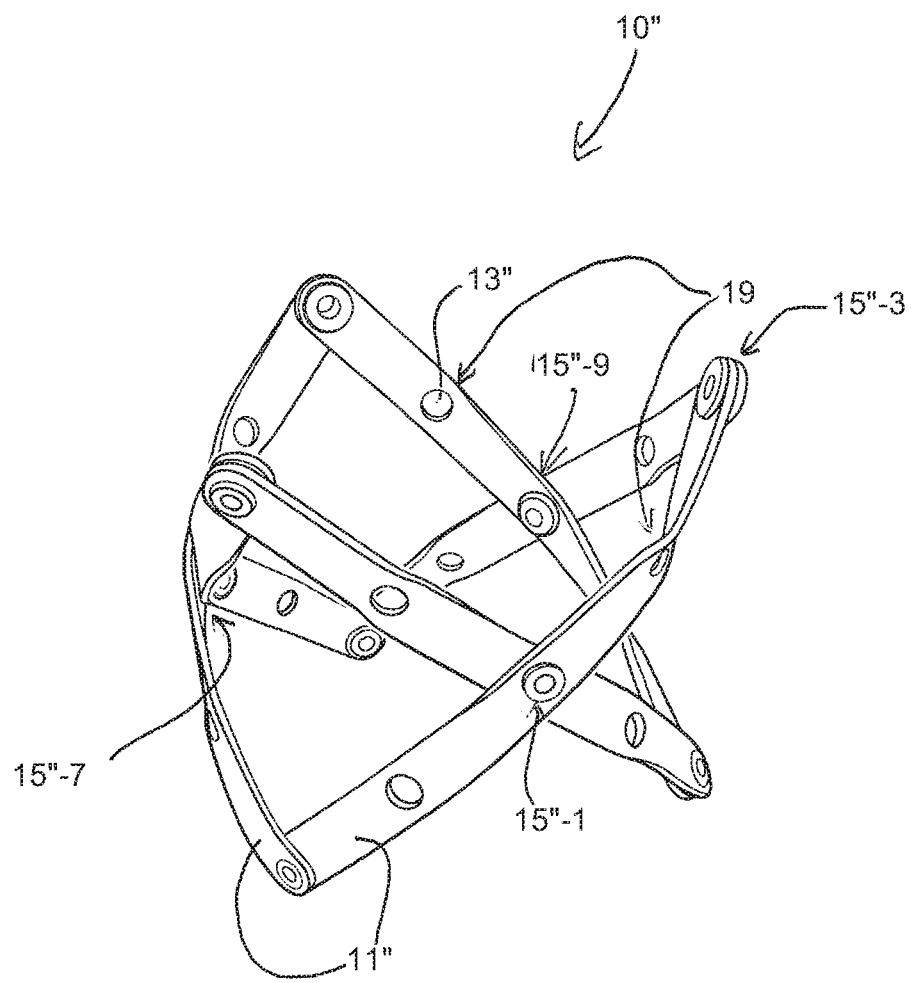
FIG. 17 is a perspective view of an hourglass-shaped support structure configuration.

FIG. 17 is a perspective view of an hourglass-shaped support structure configuration. In this configuration, the circumference around the middle pivot points 15"-1, 15"-7, 15"-9 (the waist) is less than the circumference at either end of the stent 10". As shown, the hourglass shaped support structure 10" is achieved by reducing the number of strut members 11" to six and shortening the strut members 11" in comparison to prior embodiments. As a result of the shortening, there are fewer orifices 13" per strut member 11". Because of the strut number and geometry, each strut member 11" includes a twist at points 19" along there longitudinal planes. The twists provide a flush interface between joined strut 15"-3.

An hourglass stent configuration could also be achieved by imposing concave or convex curvatures in individual bars 11". The curvature could be a property of the materials (e.g. shape-memory or heat-sensitive Nitinol). The curvature could be absent in the compressed stent state and appear when the stent is in its expanded state.

It should be noted that any of the above-described support structures can be extended beyond the anchor joints at either of both ends of the stent. By coupling a series of stents in an end-to-end chain fashion, additional stent lengths and geometries can be fabricated. In particular, an hourglass-shaped stent could be achieved by joining two cone-shaped stents at their narrow ends. The hourglass shape can also be modified by assembling the middle scissor pivots off center as shown in FIG. 14.

Particular embodiments of the invention offer distinct advantages over the prior art, including in their structure and applications. While certain advantages are summarized below, the summary is not necessarily a complete list as there may be additional advantages.

The device allows the user to advert the serious complications that can occur during percutaneous heart valve implantation. Because the device is retrievable and re-positionable during implantation into the body, the surgeon can avoid serious complications due to valve mal-positioning or migration during implantation. Examples of these complications include occlusion of the coronary arteries, massive paravalvular leakage, or arrhythmias.

The device can also decrease vascular access complications because of the device's narrow insertion profile. The device's profile is low, in part, due to its unique geometry, which allows neighboring struts in the stent to overlap during stent compression. The device's low profile is further augmented by eliminating the necessity for a balloon or a sheath. The device's narrow profile offers the advantage of widening the vascular access route options in patients. For instance, the device can enable the delivery of the prosthetic valve through an artery in the leg in a patient whom would have previously been committed to a more invasive approach through the chest wall. The device therefore aims to decrease complications associated with the use of large profile devices in patients with poor vascular access.

The tissue valve embodiments can offer improved durability by allowing for attachment of the leaflets to flexible commissural posts. The flexible posts allow dissipation of the stress and strain imposed on the leaflet by the cardiac cycle. The use of multi-ply struts enables the leaflets to be sandwiched in between the struts, which re-enforces the leaflet attachments and prevents tearing of sutures. The valve further assumes a desirable leaflet morphology, which further reduces the stress and strain on leaflets. Namely, the angled leaflet attachment to the stent is similar to the native human aortic valve's inter-leaflet trigone pattern. These properties significantly improve the longevity of percutaneous heart valve replacement therapies.

The device could reduce or eliminate arrhythmia complications due to the incremental expansion or compression of the stent. The stent can employ a screw mechanism for deployment, which enables the stent to self-lock or un-lock at all radii. This enables more controlled deployment and the potential for individualizing the expansion or compression of the device in each patient. Because the expansion or compression of the device is reversible at any stage during the procedure, the surgeon can easily reverse the expansion of the device to relieve an arrhythmia. In addition, if an arrhythmia is detected during implantation, the device can be repositioned to further eliminate the problem.

The device can reduce or eliminate paravalvular leak due to the device's ability to be accurately positioned, and re-positioned, if necessary. That can considerably decrease the occurrence and severity of paravalvular leaks.

The device eliminates balloon-related complications. The screw mechanism of deployment exploits the mechanical advantage of a screw. This provides for forceful dilation of the stent. The lever arms created by the pivoting of the struts in the scissor linkage of the stent, transmits a further expansion force to the stent. The stent is expanded without the need for a balloon. In addition, the ability of the device to be forcefully dilated reduces or eliminates the need for pre- or postballooning during the implantation procedure in patients.

The device has more predictable and precise positioning in the body because the difference between the height of the stent in the compressed and expanded position is small. This "reduced foreshortening" helps the surgeon to position the device in the desirable location in the body. The ability to re-position the device in the body further confers the ability to precisely position the device in each individual.

In addition to the mechanical advantages, the device enables a wider population of patients to be treated by a less invasive means for valve replacement. For example, the device enables patients with co-morbidities, whom are not candidates for open chest surgical valve replacement, to be offered a treatment option. The device's ability to assume a narrow profile also enables patients who were previously denied treatment due to poor vascular access (e.g. tortuous, calcified, or small arteries), to be offered a treatment option. The durability of the valve should expand the use of less-invasive procedures to the population of otherwise healthy patients, whom would otherwise be candidates for open chest surgical valve replacement. The device's ability to be forcefully expanded, or assume hourglass, or conical shapes, potentially expands the device application to the treatment of patients diagnosed with aortic insufficiency, as well as aortic stenosis.

The device can also provide a less invasive treatment to patients with degenerative prosthesis from a prior implant, by providing for a "valve-in-valve" procedure. The device could be accurately positioned inside the failing valve, without removing the patient's degenerative prosthesis. It would help the patient by providing a functional valve replacement, without a "re-do" operation and its associated risks.

While this invention has been particularly shown and described with references to particular embodiments, it will be understood by those skilled in the art that various changes in form and details may be made to the embodiments without departing from the scope of the invention encompassed by the appended claims.

I claim:

1. A prosthetic heart valve, comprising:
a tubular frame having first and second end portions, a central longitudinal axis extending between the first and second end portions, and a plurality of struts interconnected by a plurality of joints, wherein the joints comprise a rotational axis perpendicular to the longitudinal axis, wherein the frame is movable between an expanded configuration and a compressed configuration, wherein the struts comprise proximal end portions, distal end portions, and intermediate portions, wherein the proximal end portions of the struts are disposed at the first end portion of the frame and are interconnected by a first subset of joints, wherein the distal end portions of the struts are disposed at the second end portion of the frame and are interconnected by a second subset of joints, wherein the intermediate portions of the struts are disposed between the proximal and distal end portions of the struts and are interconnected by a third subset of joints, and wherein the struts comprise diagonal struts relative to the longitudinal axis when the frame is in the expanded configuration;
a valve component having a plurality of leaflets, wherein adjacent leaflets are attached together and to the frame at commissures of the frame, and wherein the leaflets extend from the commissures in a triangular configuration and are attached to adjacent diagonal struts of the frame; and
a skirt configured for reducing paravalvular leakage and attached to the diagonal struts of the frame to which the leaflets are attached.

2. The prosthetic heart valve of claim 1, wherein the leaflets and the skirt are attached to the diagonal struts of the frame with sutures.

3. The prosthetic heart valve of claim 1, wherein the commissures of the frame are formed at intersections of two diagonal struts.

4. The prosthetic heart valve of claim 1, wherein the skirt is disposed on an exterior surface of the frame.

5. The prosthetic heart valve of claim 1, wherein the skirt comprises first and second end portions, wherein the first end portion of the skirt is disposed adjacent the first end portion of the frame, and wherein the second end portion of the skirt is disposed adjacent the commissures of the frame.

6. The prosthetic heart valve of claim 1, wherein the leaflets are attached to the skirt with sutures.

7. The prosthetic heart valve of claim 1, wherein the skirt is attached to the frame with sutures that extend through openings in the struts of the frame.

8. A prosthetic heart valve, comprising:

a tubular frame having first and second end portions, a central longitudinal axis extending between the first and second end portions, a plurality of pivot joints, a first plurality of interconnected struts, and a second plurality of interconnected struts, wherein the frame is radially compressible and expandable between an expanded configuration and a compressed configuration, wherein the first plurality of struts includes inner and outer struts arranged in an alternating inner-outer pattern, the first plurality of struts being interconnected by a first subset of the pivot joints at proximal and distal end portions of the first plurality of struts, wherein the second plurality of struts includes inner and outer struts arranged in an alternating inner-outer pattern, the second plurality of struts being interconnected by a second subset of the pivot joints at proximal and distal end portions of the second plurality of struts, wherein the first and second pluralities of struts are connected by a third subset of the pivot joints disposed between the proximal and distal end portions of the first and second pluralities of struts, and wherein the first and second pluralities of struts comprise angled struts that are angled relative to the longitudinal axis when the frame is in the expanded configuration;

a valve component having a plurality of leaflets, wherein each leaflet has opposing sides that are attached to adjacent angled struts of the frame by sutures; and an annular, outer skirt configured for reducing paravalvular leakage and attached by sutures to the outside of the frame along the same angled struts of the frame to which the sides of the leaflets are attached.

9. The prosthetic heart valve of claim 8, wherein the angled struts are angled between 20-70 degrees relative to the longitudinal axis of the frame when the frame is in the expanded configuration.

10. The prosthetic heart valve of claim 8, wherein the opposing sides of each leaflet extend from an inflow edge of the leaflet toward an outflow edge of the leaflet.

11. The prosthetic heart valve of claim 8, wherein when the frame is in the expanded configuration, adjacent sides of adjacent leaflets diverge away from each other moving in a direction extending from an outflow end of the frame to an inflow end of the frame.

12. The prosthetic heart valve of claim 8, wherein the sutures extend through openings in the angled struts.

13. The prosthetic heart valve of claim 8, wherein the outer skirt is attached to the frame via sutures that extend through openings in the first and second pluralities of struts.

14. The prosthetic heart valve of claim 8, wherein the outer skirt and the sides of the leaflets are attached to the same angled struts with multiple suture loops formed along the length of the struts between their opposing ends.

15. The prosthetic heart valve of claim 8, wherein the leaflets comprises pericardial tissue, and wherein the outer skirt comprises polytetrafluoroethylene.

16. A prosthetic heart valve, comprising:

a frame having inflow and outflow ends, a central longitudinal axis extending between the inflow and outflow ends, a plurality of pivot fasteners, a first plurality of struts interconnected by a first set of the pivot fasteners, and a second plurality of struts interconnected by a second set of the pivot fasteners, wherein the first plurality of struts is interconnected to the second plurality of struts by a third set of the pivot fasteners that bisect the first and second pluralities of struts, wherein the pivot fasteners allow the first and second pluralities of struts to pivot relative to each other between an expanded configuration and a compressed configuration, and wherein the first and second pluralities of struts comprise diagonal struts that are angled relative to the longitudinal axis when the frame is in the expanded configuration;

a valve component having a plurality of leaflets, wherein each leaflet has opposing sides that are attached to adjacent diagonal struts; and an annular, outer skirt configured for reducing paravalvular leakage, wherein the skirt is attached to the outside of the frame along the same diagonal struts of the frame to which the sides of the leaflets are attached, wherein the sides of the leaflets and the outer skirt are attached to the same diagonal struts with multiple suture loops formed along the length of the diagonal struts between their opposing ends.

17. The prosthetic heart valve of claim 16, wherein adjacent sides of adjacent leaflets are arranged in pairs of leaflet sides that are attached to commissures of the frame disposed adjacent the outflow end of the frame, wherein the sides of the leaflets extend from the commissures toward the inflow end of the frame along corresponding diagonal struts.

18. The prosthetic heart valve of claim 17, wherein adjacent leaflet sides of each pair diverge away from each other in a triangular configuration from a corresponding commissure toward the inflow end of the frame.

19. The prosthetic heart valve of claim 16, wherein each of the diagonal struts extends the entire length of the frame such that the opposing ends of the diagonal struts define the inflow and outflow ends of the frame.

20. The prosthetic heart valve of claim 16, wherein the leaflets comprises pericardial tissue, and wherein the outer skirt comprises polytetrafluoroethylene.

* * * * *